US005526819A

United States Patent [19]

Lonsbury-Martin et al.

[11] Patent Number: 5,526,819

[45] Date of Patent: Jun. 18, 1996

[54] METHOD AND APPARATUS FOR DISTORTION PRODUCT EMISSION TESTING OF HEATING

[75] Inventors: Brenda L. Lonsbury-Martin; Glen K. Martin, both of Houston, Tex.

[73] Assignee: Baylor College of Medicine, Houston, Tex.

[21] Appl. No.: 296,868

[22] Filed: Aug. 26, 1994

Related U.S. Application Data

[63] Continuation of Ser. No. 64,356, May 18, 1993, abandoned, which is a continuation of Ser. No. 471,106, Jan. 25, 1990, abandoned.

[51] Int. Cl.[6] .................... G06F 159/00

[52] U.S. Cl. .................... 128/746

[58] Field of Search .................... 367/413.02; 128/746; 73/585, 587; 381/54

[56] References Cited

U.S. PATENT DOCUMENTS

| | | | |
|---|---|---|---|
| 4,374,526 | 2/1983 | Kemp | 128/746 |
| 4,459,996 | 7/1984 | Teele | 128/746 |
| 4,589,137 | 5/1986 | Miller | 381/94 |
| 4,630,304 | 12/1986 | Borth et al. | 381/94 |
| 4,636,586 | 1/1987 | Schiff | 379/390 |
| 4,649,505 | 3/1987 | Zinser, Jr. et al. | 379/411 |
| 4,653,102 | 3/1987 | Hansen | 381/92 |
| 4,672,674 | 6/1987 | Clough et al. | 381/71 |
| 4,684,989 | 8/1987 | Roeder | 358/167 |
| 4,716,907 | 1/1988 | Nakamura | 128/731 |
| 4,884,447 | 12/1989 | Kemp et al. | 73/585 |
| 5,033,082 | 7/1991 | Eriksson et al. | 379/410 |
| 5,267,571 | 12/1993 | Zurek et al. | 128/746 |

OTHER PUBLICATIONS

*Journal of Acoustical Society of America*, vol. 78, No. 5, Nov. 1985, Horner, et al., "Distortion Product Otoacoustic Emissions in Hearing–Impaired Mutant Mice", (Abstract Only).

*J. Otolaryngol.*, vol. 18, No. 7, 1989, Kimberley et al., "Distortion Product Emissions and Sensorineural Hearing Loss" (Abstract Only).

*Hear Ros.*, Jan. 1984, vol. 13, No. 1, Brown et al., "Suppressibility of the 2f1–f2 Stimulated Acoustic Emissions in Gerbil and Man" (Abstract Only).

D. T. Kemp, Stimulated acoustic emissions from within the human auditory system. Journal of Acoustical Society of America; vol. 64; pp. 1386–1391; Nov. 1978.

D. T. Kemp, Evidence of Mechanical Nonlinearity and (List continued on next page.)

*Primary Examiner*—Donald McElheny, Jr,
*Assistant Examiner*—Frantzy Poinvil
*Attorney, Agent, or Firm*—Bush, Moseley, Riddle & Jackson

[57] ABSTRACT

Apparatus and method are disclosed for the recording of distortion product emission (DPE) levels in human beings. At least one microphone and a sound-delivery system is inserted in the external ear canal in a manner similar to that required to position a small hearing aid. Two primary tones $T_{f1}$, $T_{f2}$ are applied simultaneously to the ear. The cochlea of the inner ear produces a DPE tone which is sensed by the microphone. DPE levels are sensed as a function of input frequencies $f_1$ and $f_2$. Such DPE frequency is equal to $2f_1-f_2$. Such DPE frequencies are collected in 100 Hz steps by adjusting $f_1$ and $f_2$ and maintaining a substantially constant ratio between $f_1$ and $f_2$. Two output forms are created: an DPE audiogram and a DPE input/output function. Noise picked up by the microphone is reduced by averaging the DPE signal many times, yet causing each of the DPE signals that is averaged to be of the same phase as every other DPE signal. Random phase noise is reduced by the averaging process. Body noise may be reduced by using two microphones and applying the output of one such microphones to the plus input of a differential amplifier. The output of the other less sensitive microphone, after amplification and phase adjustment is applied to the negative input of such differential amplifier. The output of such amplifier results with the body noise signal substantially reduced, but with the DPE signal substantially unchanged. This abstract of the disclosure-is not intended to define the scope of the invention.

13 Claims, 6 Drawing Sheets

OTHER PUBLICATIONS

Frequency Selective Wave Amplification in the Cochlea; Archives of Otorhinolaryngology; vol. 224; pp. 37–45; 1979.

Kemp, Bray, Alexander, Brown; Acoustic Emission Cochleography–Practical Aspects; Scand Audial Suppl.; vol. 25; pp. 71–95; 1986.

Bray and Kemp, An advanced cochlear echo technique suitable for infant screening; British Journal of Audiology vol. 21, pp. 91–204; 1987.

Harris, Lonsbury–Martin, Stagner, Coats, Martin; Acoustic distortion products in humans: Systematic changes in amplitude as a function of $f_2/f_1$ ratio; J. Acoustic Society of America; vol. 85; pp. 220–229; exact date unknown, Jan. 1989 printed on copy of paper.

Schmiedt, Acoustic Distortion in the ear canal, I. Cubic different tones: Effects of acute noise injury; J. Acoustic Society of America; vol. 79(5) pp. 1481–1490; May 1986 (date printed on publication).

Schmiedt et al, Ear–canal acoustic emissions as frequency, –specific indication of cochlear function; J. Acoustic Society of America Supplement 1; vol. 72 p. 56; Fall, 1982, Kemp and Brown; An Integrated View of Cochlear Mechanical Nonlinearities Observable from the Ear Canal; unknown publication, volume, page and date.

D. T. Kemp; Otoacoustic emission, traveling waves and cochlear mechanism; Hearing research (Elsevier Science Publishers B.V. (Biomedical Div.)); vol. 22; pp. 95–104; 1986.

Schmiedt; Acoustic injury and the physiology of hearing; J. Acoustic Society of America; vol. 76(5); pp. 1293–1317; Nov. 1984 (printed on pages).

FIG. 3B
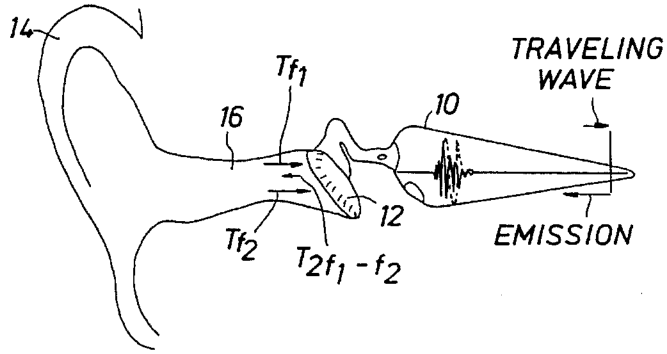
FIG. 3C
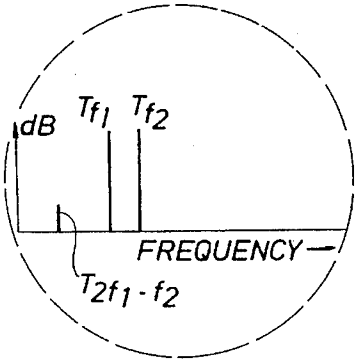
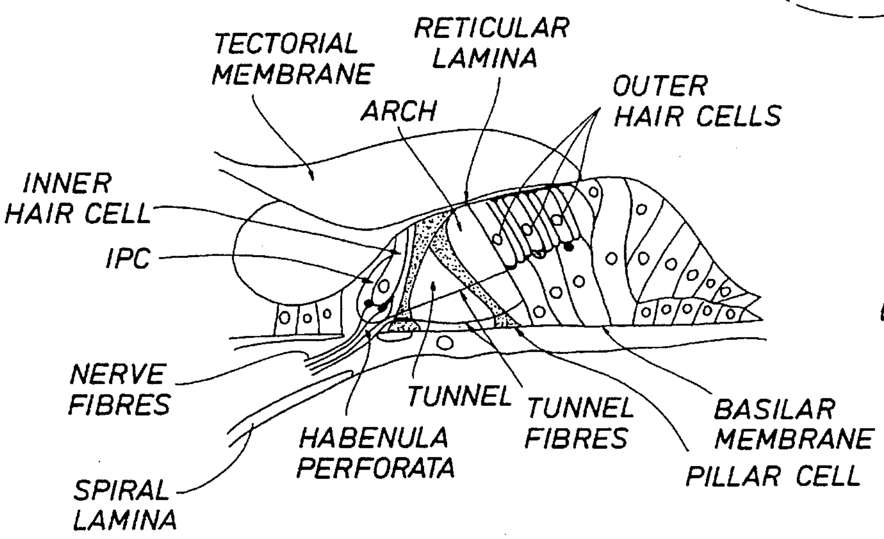
FIG. 4
(PRIOR ART)
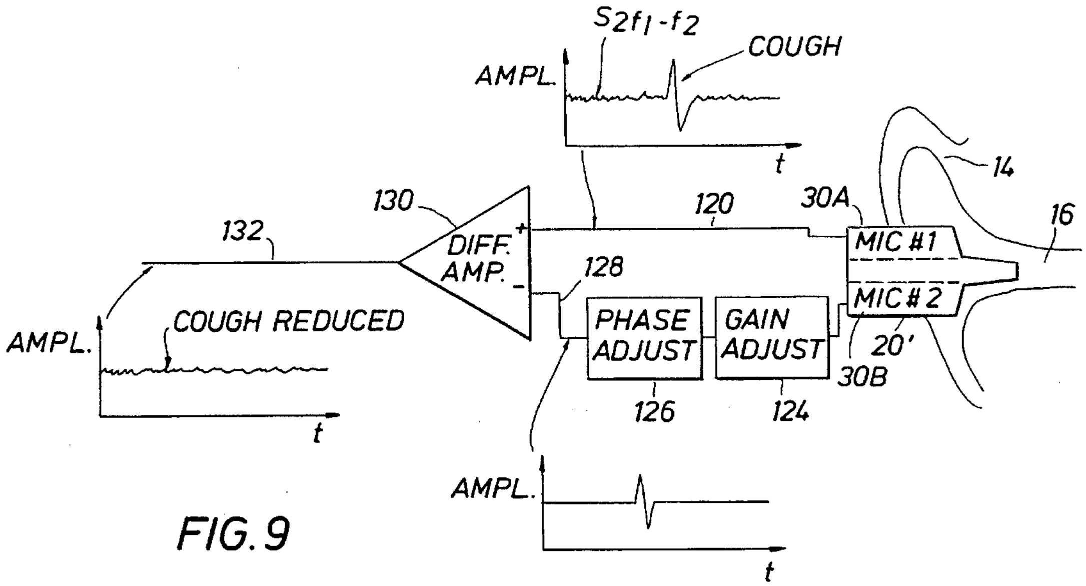
FIG. 9

METHOD AND APPARATUS FOR DISTORTION PRODUCT EMISSION TESTING OF HEATING

U.S. GOVERNMENT SUPPORT

The invention described and claimed herein resulted from work supported by U.S. government grants from the National Institutes of Health. The Government has certain right in the invention.

This application is a continuation of application Ser. No. 08/064,356 filed May 18, 1993 now abandoned, which is a continuation of Ser. No. 07/471,106 filed Jan. 25, 1990 now abandoned.

BACKGROUND

1. Field of the Invention

This invention relates in general to hearing testing of a human being. In particular, the invention relates to recording of distortion product emissions (DPEs) of human ears. Still more particularly, the invention relates to apparatus and methods for recording DPE audiograms and input/output functions and to the minimization of random noise in the presence of DPE.

2. Description of the Prior Art

Otoacoustic Emissions (OAEs), first described in 1978, represent acoustic energy presumed to be generated by stimulus-induced, motile activity of the outer hair cells of the Organ of Corti in the Cochlea of the inner ear of a human being and other mammals. It is believed that mechanical feedback of such outer hair cells into basilar membrane motion and their related cochlear-efferent endings are part of a biomechanical gain system that is responsible for the sharp tuning and high sensitivity associated with normal hearing.

Otoacoustic emissions (OAEs) may be classified generally as spontaneous emissions and "evoked" or stimulated emissions. Stimulated emissions can be further separated into three subclasses consisting of transiently evoked emissions (TEEs), stimulus-frequency emissions (SFEs), and distortion-product emissions (DPEs). Each type of stimulus [i.e., clicks (TEEs) or low-level, continuous pure tones (SFEs) or continuous, simultaneously applied, two-tone stimuli (DPEs)] generates evoked emissions. TEEs and SFEs have an appreciable latent or delayed time period with respect to stimulus onset. DPEs, have a nonlatent or instantaneous onset. Based on the response-latency distinction, it is believed that separate subcellular components of the outer hair cell support the generation of delayed versus instantaneous evoked OAEs. For example, the stimulus-induced movements of the stereocilia bundle likely generate the nonlatent DPEs, while the motile activity of the lateral regions of the hair-cell membrane likely produces the latent TEEs and SFEs.

D. T. Kemp proposed that a transient OAE could be a diagnostic tool in the examination of impaired hearing. Kemp, *Stimulated Acoustic Emissions from within the Human Auditory System,* J. Acoust. Soc. Am., Vol 64, No. 5, pp 1386–1391, November 1978. After Kemp's discoveries became known to the art of hearing research, a number of researchers investigated the status of stimulated OAEs in people with normal hearing and with hearing impairments.

Early studies established that emissions are present in essentially all normally hearing individuals and that such emissions are reduced or eliminated in regions of sensorineural hearing loss. Moreover, it became apparent that, of the three types of stimulated emissions, SFEs could not be simply applied in practical settings, because they require the utilization of complex methods of analysis in order to separate them from the eliciting stimulus.

Of the remaining evoked-emission types, that is TEEs and DPEs, TEEs have received, by far, the most attention as potential clinical measures of cochlear function. The development of transiently evoked otoacoustic emissions (TEEs) has, in fact, reached an advanced level in that a computer-based commercial device is currently available to the audiologist: D. T. Kemp, et al., *Acoustic Emission Cochleography—Practical Aspects,* Scand Audial Suppl. 25, pp. 71–95, 1986; Peter Bray and David Kemp, *An Advanced Cochlear echo Technique Suitable for Infant Screening,* British Journal of Audiology, 1987, No. 21, pp. 191–204.

The form of a TEE from a given ear is subject to the invariable influence of fixed-frequency emissions that are unique to that ear. In the presence of idiosyncratic frequencies, including the spontaneous and stimulus-frequency otoacoustic emissions, as well as the TEEs themselves, cochlear function, at specific frequencies (e.g., audiometric-test frequencies), cannot be uniquely assessed. Consequently, TEE testing appears most useful as a screening device for estimating the absence or presence of reasonably normal hearing.

In contrast to the significant attention that TEEs have received as potential clinical indicators of outer hair-cell cochlea function, DPEs have not been extensively investigated as the basis of an objective test of hearing impairment.

3. Identification of Objects of the Invention

In view of the inherent problems of using TEEs and SFEs for hearing testing, it is a general object of the invention to provide method and apparatus for using DPEs as the basis of an objective hearing test, both for normal and hearing-impaired ears.

It is another object of this invention to provide a method and apparatus by which an ear may be tested, using DPEs, for hearing capability at any frequency between approximately one and eight kHz. In other words, it is an object of this invention to provide a method and apparatus for creating a DPE audiogram for a human being.

It is another object of this invention to provide a method and apparatus by which an objective measure of the hearing capability at a particular frequency varies as a function of stimulus level, so as to permit a complete evaluation of cochlear function at both threshold and suprathreshold levels of stimulation. In other words, it is an object of the invention to provide a method and apparatus for creating a DPE input/output function for a human being.

It is another object of this invention to provide a method and apparatus by which DPEs may be used to evaluate remaining outer hair-cell function in hearing impared human beings having a hearing loss up to 45–55 dB HL.

It is another object of this invention to provide noise reduction method and apparatus for reducing the noise signal which contaminates the measurement of the DPE, thereby providing a system which may be used in a noisy environment such as a doctor's clinic or other hearing screening facility.

SUMMARY OF THE INVENTION

To produce DPEs, two related pure tones are simultaneously presented to the ear. Such tones usually, (but not necessarily required) are of equal amplitude. The non-linear response to such tones, believed to occur in the cochlea of the inner ear, generate a lower amplitude tone in the ear. Such tone, believed to be produced by biomechanical elements of the cochlea, is at a frequency lower than the frequency $f_1$ or $f_2$ of the two input tones. Such DPE tone is at a frequency of $2f_1-f_2$, but its amplitude is considerably lower than the amplitude of the two input tones at frequencies $f_1$ and $f_2$.

This invention includes providing first and second tones of respective frequencies $f_1$ and $f_2$ to the ear canal of the outer ear. Such tones are provided to an eartip via earphones driven by a signal generator. Such eartip includes at least one microphone for sensing not only the two input tones at frequencies $f_1$ and $f_2$, but also the DPE tone at frequency $2f_1-f_2$. The microphone electrical signal output is amplified and then applied to a spectrum analyzer which produces, a signal output representative of the level of each frequency in the spectrum of frequencies of such microphone electrical signal output.

According to one aspect of the invention, a programmed digital computer controls the generation of the input tones and the recording of levels of the various frequencies received from the microphone electrical signal output of the spectrum analyzer. Over a frequency range such as 1 kHz to 8 kHz, input tones are generated and responses recorded by the frequency analyzer. A DPE audiogram is graphically presented by one of a plurality of ways, e.g. on graph paper, on a CRT screen, or in tabular form. Such DPE audiogram may graphically be presented on x-y axes with the response frequency of the DPE tone, $2f_1-f_2$, plotted as the geometric mean of such two frequencies along the x-axis of the graph. The level of each such frequency, presented in decibels, is plotted along the y-axis of the graph. The response of normal ears may be superimposed on such graph to give the hearing clinician an objective view of the DPE amplitude versus frequency response of the patient being tested as compared to a person of normal hearing. The apparatus and method for DPE audiogram testing is advantageous over traditional hearing tests in that the procedure is completely objective, that is, it does not require a patient to respond as to whether or not a test tone has been "heard" by such patient.

According to another aspect of the invention a programmed digital computer controls the generation of the input tone at particular input frequencies $f_1$, $f_2$. The input tones, having equal amplitudes, are varied in amplitude over a predetermined range, e.g., 25 to 85 db SPL. For each input amplitude, the DPE response amplitude at frequency $2f_1-f_2$ is recorded after measurement by the frequency analyzer described above. An input/output response for the particular DPE frequency response, usually represented as the geometric mean of $f_1$ and $f_2$, is graphically plotted, either on graph paper or on a CRT screen, or is displayed in tabular form. The input amplitude in db SPL in plotted along the x-axis; the DPE amplitude is plotted along the y-axis. The "noise floor" as measured by the frequency analyzer may also be presented on the graphical display, along with a "band" of output responses which have been determined to be "normal" as a function of input amplitude. The advantage of this DPE procedure over other kinds of stimulated emission testing, is that DPEs have a reasonably wide dynamic range, in terms of growth of response amplitude as a function of stimulus level, thereby permitting evaluation of cochlear function at both "threshold" and suprathreshold levels of stimulation.

According to another feature of the invention, methods and apparatuses are provided for reducing the level of background noise sensed in DPE detection. A first method and apparatus, called phase-locked DPE extraction, initiates averaging of the DPE signal from the ear canal only when such DPE signal is at a particular phase. This method assures that all of the DPE signal is added to the averaged waveform, but background noise is significantly reduced.

According to another feature of the invention, a method and apparatus for reducing the level of background sensed in DPE detection includes providing two microphones in the eartip by which tones in the ear canal are sensed. The output of the first microphone includes signals representative of the DPE tone as well as patient-induced noise, such as coughing. The output of the second microphone is adjusted such that signals of the DPE tone are not present, yet signals representative of patient induced noise are produced. When applied to the plus and minus inputs of a differential amplifier, the output of such amplifier includes the DPE signal, with a "body" or noise signal significantly reduced due to the subtraction of the two signals.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 3B is a schematic diagram illustrating tones $T_{f1}$ and $T_{f2}$ being applied to the ear drum membrane, where they enter the organ of Corti as a traveling wave, which produces a Distortion Product Emission tone of frequency $2f_1-f_2$ which is transmitted by the middle ear ossicles to the ear drum membrane, which vibrates like a speaker diaphram to transduce the DPE into acoustic energy in the ear canal;

FIG. 3C is an illustration showing the relative frequencies and amplitudes of the stimulating tones and the DPE tone which is generated by the cochlea;

FIG. 4 is a more detailed illustration of a cross-section of the Organ of Corti of the cochlea, in which may be seen the outer hair cells and the inner hair cells with nerve fibers connected thereto;

FIG. 7A is a traditional audiogram for a hearing impared person, while

FIG. 9 schematically illustrates a two-microphone embodiment of the apparatus by which body noises such as coughs and the like may be minimized during the measurement of the DPE signal.

DESCRIPTION OF THE INVENTION

This invention relates to apparatus and methods for measuring Distortion Product Emission (DPE) tones which are generated in the ear in what is believed to be a non-linear bio-mechanical feedback mechanism of the cochlea of an ear. By inducing such DPE tones, analyzing the level of such tones with respect to input tones, minimizing the noise associated with such tones, and presenting recorded tones in audiogram and input/output displays, hearing of a human being can be objectively assessed.

In order to introduce the basis for the apparatus and method of the invention, FIGS. 1, 2, 3A, 3B and 4 illustrate the physiology of the hearing process of a human being.

Figure 1:
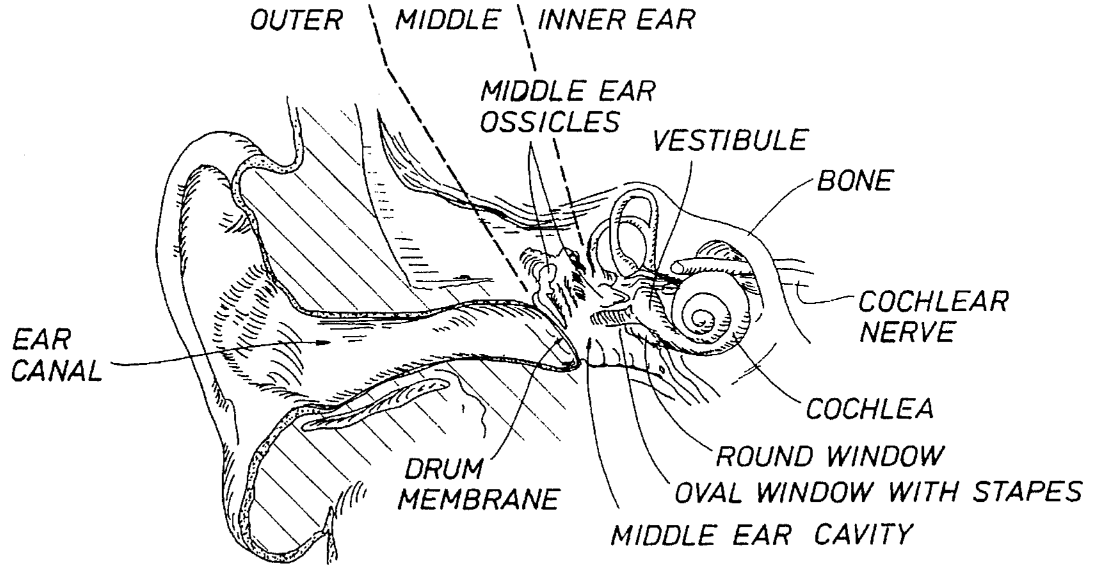
FIG. 1 is a prior art illustration of a cross-section through a human ear showing outer, middle and inner ear parts with the cochlea of the inner ear responding to tones transmitted to the middle ear, generating nerve signals via the cochlear nerve.

FIG. 1 shows a partial cross-section through a human ear with the outer, middle and inner sections of the ear illustrated. The ear canal is a passage in the outer ear which terminates with an ear drum membrane. Sound in the form of air pressure vibrations of multiple frequencies and amplitudes cause the ear drum membrane to vibrate.

Figure 3A:
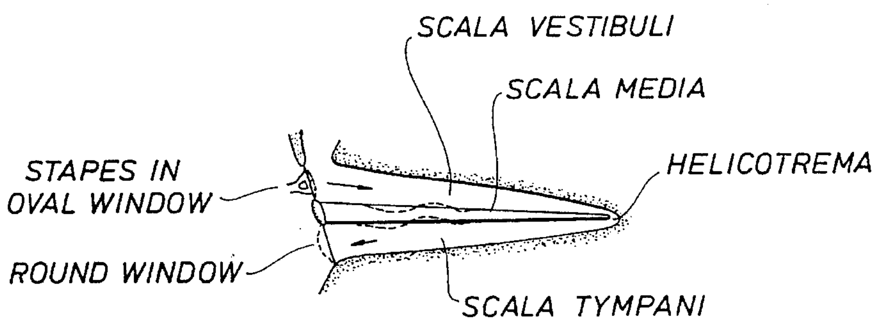
FIG. 3A is a schematic diagram of the cochlea depicted as unrolled, with a tone entering the oval window and stapes and traveling via the scala vestibuli and back via the scala tympani, while vibrating the scala media with its Basilar membrane and the Organ of Corti.

Disposed in the middle ear cavity, are ossicles, small boney structures which oscillate in response to the oscillations of the drum membrane. As shown in FIG. 3A the stapes ossicle terminates at the oval window of the cochlea of the inner portion of the ear.

Figure 2:
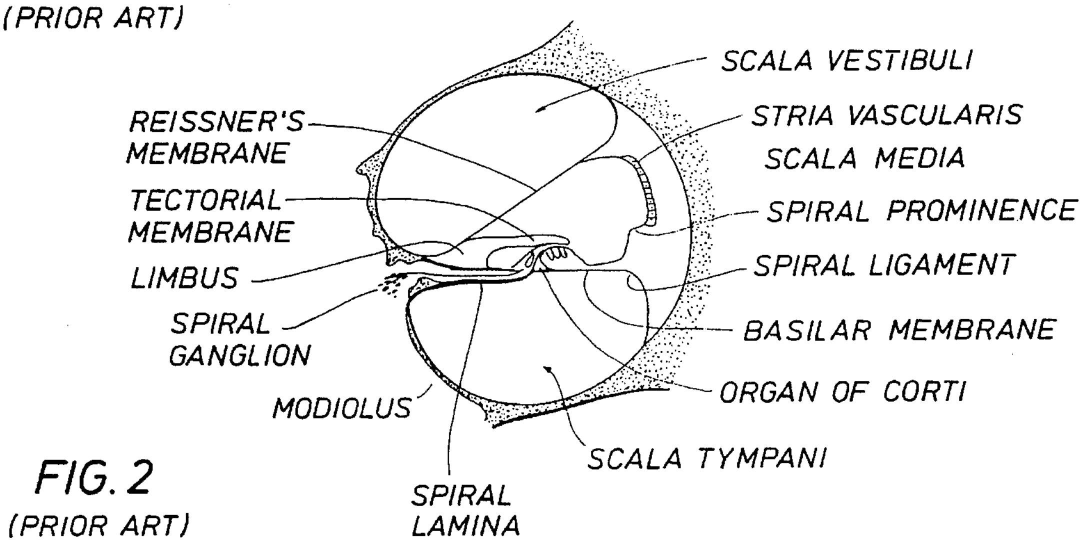
FIG. 2 is a prior art illustration of a cross-section through one portion of the cochlea, showing the placement of the Organ of Corti along the spiral of the cochlea.

The cochlea (see FIGS. 1, 2, 3A, 4) is a spiral or snail like structure of the inner ear. It is a bio-mechanical organ for transforming oscillations of the stapes and the fluid of the cochlea into nerve impulses for recognition by the brain. FIG. 2 shows a cross-section through a portion of the cochlea. FIG. 3A shows a schematic diagram of an "unrolled" cochlea illustrating a sound wave entering the oval window and causing the scala media to oscillate as the sound pressure traverses the scala vestibuli and the scala tympani. As illustrated in FIG. 2, the Organ of Corti is disposed on the basilar membrane of the scala media. Accordingly, vibrations or oscillations of the scala media in response to air pressure vibrations via the outer ear canal and the vibration of the ear drum membrane, cause the Organ of Corti to vibrate. As illustrated in FIG. 4, the Organ of Corti has inner and outer hair cells disposed along the entire spiral length of the cochlea. Each inner hair cell includes nerve fibers which lead to the brain.

FIG. 3B illustrates the Distortion Product Emission phenomenon. When two audio tones are applied to the outer ear canal, such tones are simultaneously applied to the cochlea as traveling waves. Such tones, one of lower frequency $f_1$, the other of higher frequency $f_2$, are preferably applied with equal amplitude, or $f_1$ 10–15 dB larger than $f_2$, and of a frequency ratio $f_2/f_1$ of about 1.21. Under such conditions a healthy human cochlea 10 generates a lower frequency, lower amplitude tone which is sensed by the ear drum 12. FIG. 3B schematically illustrates that such tone in a human being is at a frequency of $2f_1-f_2$.

It has been discovered, as a result of tests in both normal and hearing impared ears with a number of human beings, that DPEs can form the basis of an objective hearing test. DPE testing has several advantages over the use of Transiently Evoked Emission (TEE) testing. In particular, because of the continuous, short-latency nature of the DPE, essentially any frequency, between approximately 1 and 8 kHz, can be intentionally tested. Such frequency specificity indicates that a DPE "audiogram", objectively produced, can be a substitute for, or an adjunct to a conventional audiogram, where the patient subjectively responds to tones at different frequencies and amplitudes or levels.

Moreover, it has been discovered that compared to other stimulated-emission types of responses of the human ear, the reasonably wide dynamic range of DPEs, in terms of increase of response amplitude as a function of stimulus level, permits evaluation of cochlear function at both threshold and suprathreshold levels of stimulation. This latter feature allows the use of DPEs to evaluate remaining outer hair-cell cochlear function in the ears of patients demonstrating a hearing loss up to 45–55 dB HL. In contrast, TEEs cannot typically be measured in individuals with hearing losses greater then 20–30 dBHL.

To produce DPEs, two related pure tones (e.g., $f_2/f_1=1.21$ or 1.22) are simultaneously presented to the ear. The nonlinear audio response, that is distorted primarily in frequency, is believed to be generated by active, biomechanical elements of the cochlea. In particular, these nonlinear elements react to the two-tone signal so that DPEs of additional, different frequencies are created. In human ears, the predominant DPE is generated at the frequency value defined by the simple algebraic expression $2f_1-f_2$. The testing for DPEs differs from the examination of TEEs in that the emissions are extracted by spectral averaging of the ear-canal signal. The spectral analysis includes emissions not only at the distortion-product frequency, but also at the frequencies of the two stimulating or primary tones, at $f_1$ and $f_2$.

Figure 5:
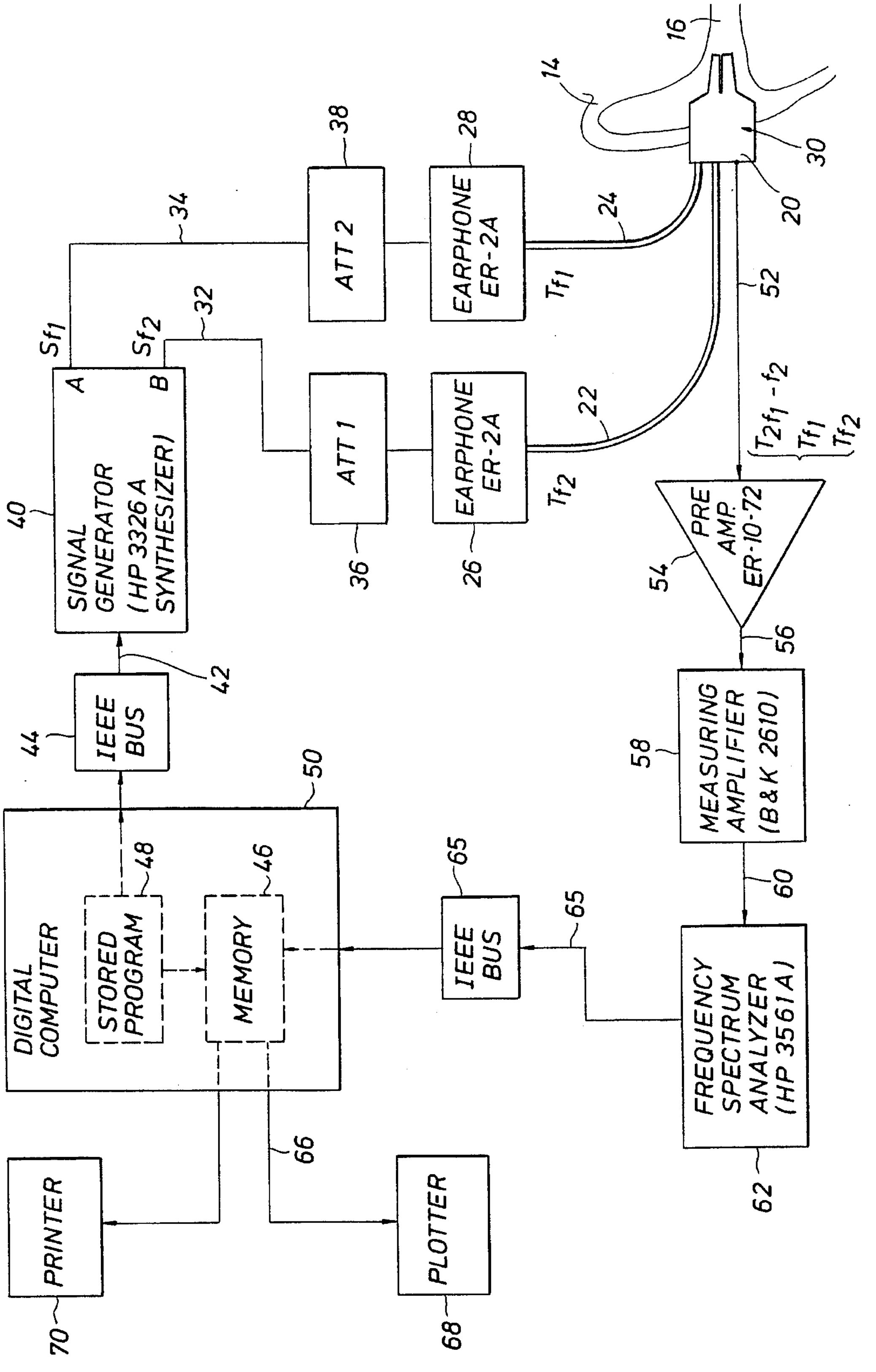
FIG. 5 is a system diagram of the apparatus necessary to produce DPE audiograms and input/output displays for assessing the hearing of a patient.

FIG. 5 illustrates, by means of a system diagram, the application of equi-level tones to the ear canal 16 of a human ear 14. A foam eartip 20 is placed in the ear canal 16. Two air ways 22, 24 are connected respectively between earphones 26 and 28 and eartip 20. The earphones or speakers 26, 28 are preferably model ER-2 speakers of Etymotic Research Corporation. Such earphones have reasonably flat responses from about 200 Hz to about 10 kHz.

The ear tip 20 also includes at least one microphone 30 which is a low-noise, miniature-microphone. Such microphone 30 is preferably model ER-10 13 of the above-mentioned Etymotic Research Corporation. It is specially designed to record low amplitude audio emissions from the human ear canal.

As illustrated in FIG. 5, a digital computer 50 preferably a Digital Equipment Computer 11/23 (but any suitable microprocessor such as an IBM PC, or equivalent may be used), is programed to step through a plurality of predetermined frequency pairs at predetermined levels or amplitudes. As mentioned above, because of the physiology of the human ear, a frequency ratio of $f_2/f_1$ is preferably about 1.21 or 1.22. The preferred levels of such frequency tones will be discussed below in conjunction with the generation of input/output plots.

Under control of the stored program 48 in computer 50, a control signal is sent to signal generator 40 via an IEEE instrumentation bus 44 and lead 42. Signal generator 40 is preferably a dual channel HP3326A synthesizer which produces, on command from computer 50, two equal level sinusoidal electrical signals on leads 32 and 34. Attenuators 36 and 38 advantageously may be placed in leads 32 and 34 between earphones 26, 28 and signal generator 50, to provide a means to precisely control the level of the primary tones, $T_{f1}$ and $T_{f2}$ applied to earphones 26 and 28 and via eartip 20 to ear canal 16. (Such attenuators preferably are Wavetek 5P programmable attentuators.)

The microphone 30 of eartip 20 is connected to preamplifier 54 via lead 52. Pre-amplifier 54 is preferably an Etymotic Research model ER-10-72. The DPE tone $T_{2f1-f2}$ as well as tones $T_{f1}$ and $T_{f2}$ from the ear canal 16 are amplified by preamplifier 54 and then applied to measuring amplifier 58, a Bruel and Kjaer model 2610. Next, such tones are applied to frequency spectrum analyzer 62, preferably a Hewlett Packard model 3561A, where the amplitude level of each tone signal is determined in decibels SPL. Such levels, as well as the frequencies of the input tones, $f_1$ and $f_2$, and the DPE tone $2f_1-f_2$ are applied to computer 50 memory 46 via lead 64 and IEEE instrumentation bus 65. Note: (IEEE signals are digital.)

Figure 6A:
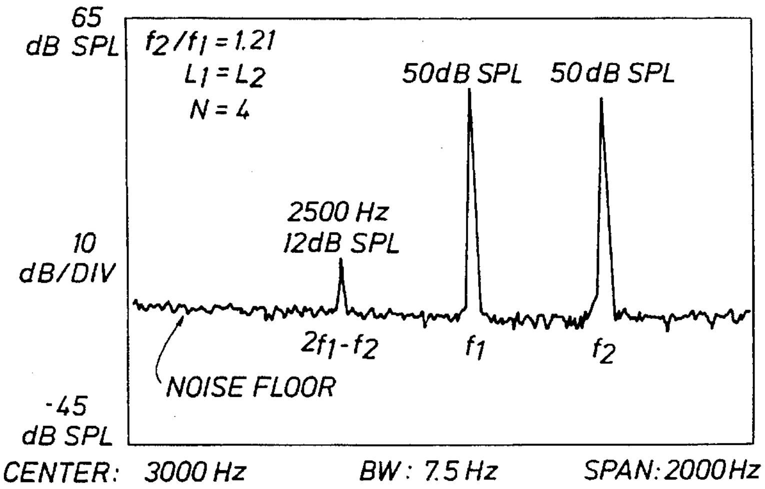
FIGS. 6A, B, C and D illustrate outputs of each DPE signal from the spectrum analyzer (6A) which are stored in computer memory (6B) and then are plotted as a DPE audiogram (6C) or as a DPE input/output display (6D).
Figure 6B:
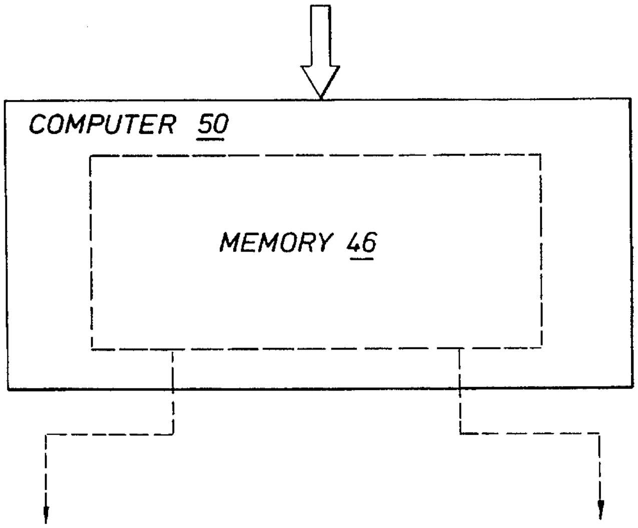

FIGS. 6A and 6B schematically illustrate the storage of the tone levels of tones $T_{2f1-f1}$, $T_{f1}$ and $T_{f2}$. The level of the noise floor is also stored.

It has been determined that the primary cochlear frequency position that contributes to the generation of the DPE at $2f_1-f_2$ is the frequency region near the geometric mean of frequencies $f_1$ and $f_2$. The geometric mean of two frequencies $f_1$ and $f_2$ is $(f_1 \times f_2)^{1/2}$. Accordingly, the levels of DPE frequencies $2f_1-f_2$ are stored in memory and plotted as described below as a function of the geometric mean frequency, $f_{geo}=(f_1 \times f_2)^{1/2}$.

According to this invention, DPE activity of a human being is specified in terms of two response measures. In the first form, illustrated at FIG. 6C, the frequency extent of cochlear function is expressed in terms of DPE amplitude as a function of stimulation frequency. Such a graphical display is called a DPE "audiogram". To obtain an objective DPE audiogram, DPEs are recorded, using the apparatus of FIG. 5, in 100 Hz steps, at three primary tone levels of 65, 75, and 85 dB SPL. The frequency ratio of the $f_1$ and $f_2$ tones are adjusted to be about 1.22 or 1.21, i.e., $f_2/f_1=1.21$ or 1.22.

Figure 6C:
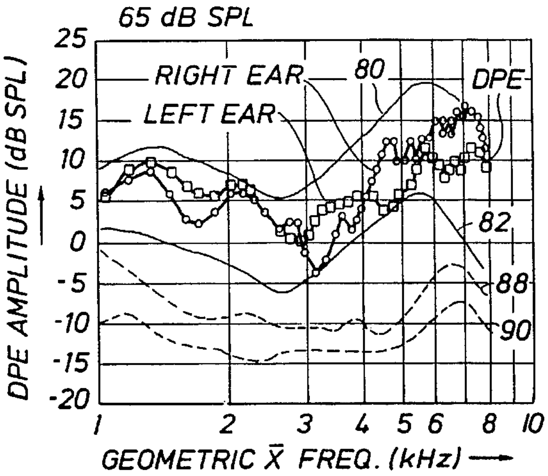
Figure 6D:
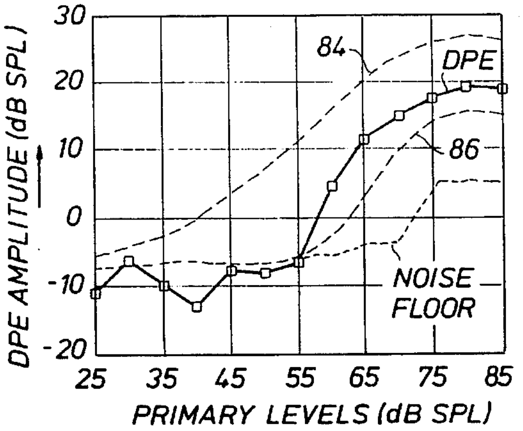

The second measure of DPE activity is shown at FIG. 6D which indicates the response/growth or input/output (I/O) aspects of DPE activity. To determine the dynamic range of the distortion-generation process, the I/O functions are determined over a 60 dB range of stimulus levels, (i.e., from 25 to 85 dB SPL). Such functions are preferably acquired at 11 discrete test frequencies, distributed in regular, ¼ octave intervals, from 1–8 kHz. The display of FIG. 6D is for one particular test frequency and shows the level response of the DPE tone as a function of increasing input tone amplitude. From the various I/O curves at the various test frequencies, information concerning the function of an ear under test can be determined. Specifically, an ear's outer hair cells at either threshold or suprathreshold sound levels can be determined.

One of ordinary skill in the digital programing art can rapidly prepare a stored program 48 and data arrangement for memory 46 to automatically collect the data for an audiogram like that of FIG. 6C and Input/Output response like that of FIG. 6D. The source code program used in a laboratory setting during the creation of this invention is attached hereto as appendix A. Such program is written in Fortran language. As indicated above, such program controls a DEC mini-computer, but the ultimate commercial version of the system of FIG. 5 will likely include a dedicated microcomputer with a stored program similar to that of Appendix A for collecting data for DPE audiograms and I/O functions.

Returning now to a more detailed explanation of the DPE audiogram of FIG. 6C, the amplitude vs. frequency bands 80, 82 represent the ±one standard deviation of a database of human DPE response as a function of DPE frequency (geometric mean of $f_1$ and $f_2$). Such bands were determined from "audiograms" of 44 ears displaying normal aural-acoustic immittance and hearing sensitivity. In FIG. 6D, bands 84 and 86 represent I/O ±one standard deviation bands at a particular frequency of such database. The noise floor of FIG. 6D represents the noise floor illustrated in FIG. 6A as recorded for the various input levels of tones $T_{f1}$ and $T_{f2}$. The bands 88, 90 of FIG. 6C represent ±one standard deviation of the noise floor.

Figure 7A:
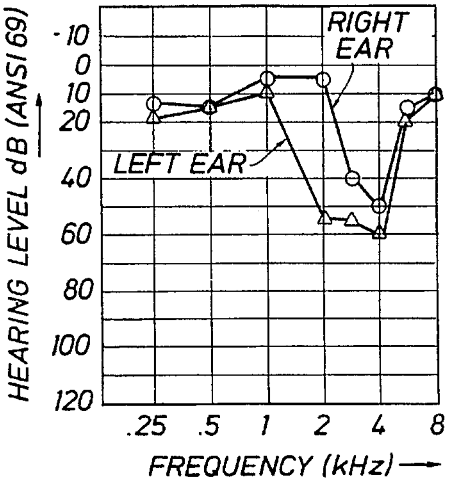
Figure 7B:
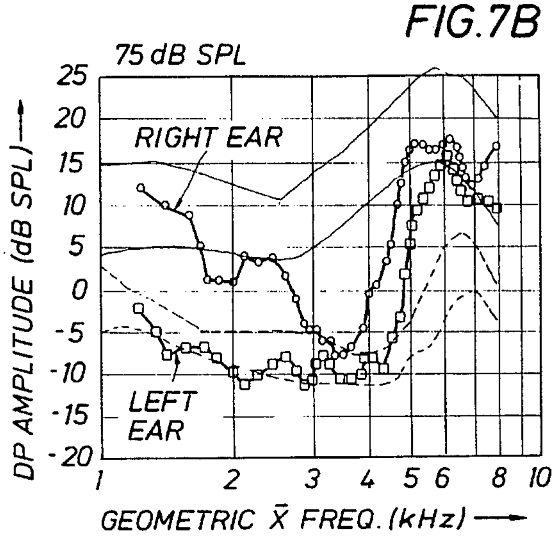
FIG. 7B is a DPE audiogram according to the invention of such person.
Figure 7C:
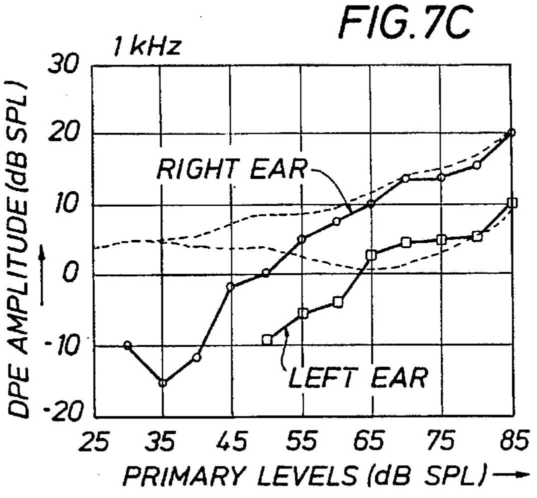
FIGS. 7C–7F are DPE input/output functions for such person.
Figure 7D:
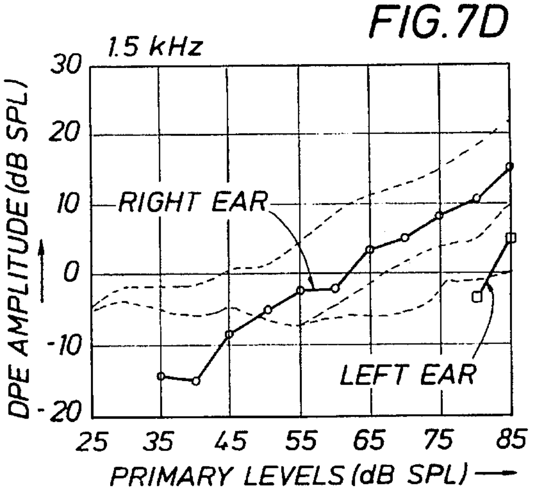
Figure 7E:
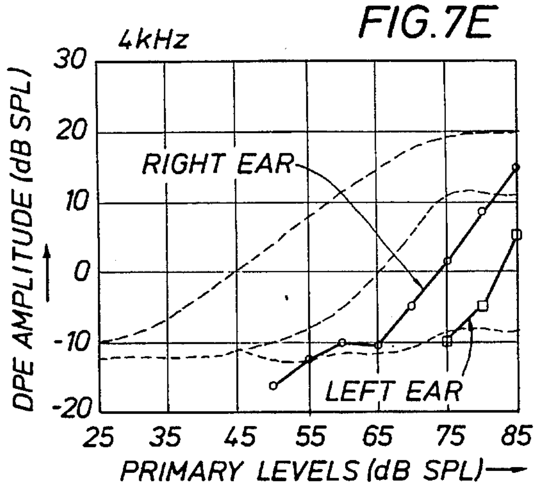
Figure 7F:
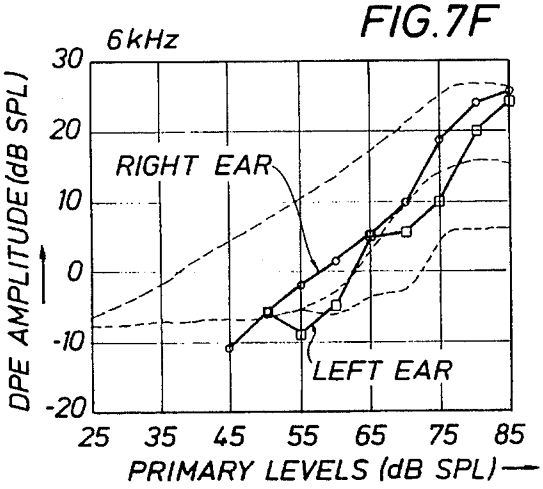

One advantage of DPE testing is that DPE emissions have the capability of accurately delimiting the boundary between normal and abnormal function. This property is illustrated best in patients exhibiting the effects of noise damage in which discrete notches and sharp reductions in high-frequency hearing commonly occur. FIGS. 7A through 7F are test results of a patient with noise-induced hearing loss due to the excessive use of recreational firearms. The standard audiograms, for each ear, are shown at FIG. 7A At FIG. 7B, the corresponding DPE "audiograms," in response to 75-dB SPL primaries, are shown. A comparison of the DPE audiogram of FIG. 7B with that of a standard audiogram of FIG. 7A indicates that the frequency pattern of the reduction in DPE amplitudes follows very closely the details of the hearing loss depicted by standard audiometrics. That is, the function for the more damaged left ear (triangular and square symbols) declined to the level of the noise floor at a frequency that was lower than that at which the curve for the better-hearing right ear (circular symbols) descended to these levels. In addition, the finer-frequency steps of the DPE "audiogram" demonstrate that the emissions for the right ear also returned to the average range of amplitudes, at a frequency that was lower in value than that at which the responses recorded from the poorer-hearing left ear reached normal emission levels.

FIGS. 7C through 7F represent several I/O functions selected to show the outcome of the discrete-frequency, I/O testing, between 1 and 6 kHz. For example, as expected from the behavioral threshold estimated for 1.5 kHz (i.e., by interpolating between 1 and 2 kHz on the behavioral audiogram), DPE magnitudes for the right ear are within normal limits. In contrast, the left ear exhibited an estimated hearing loss between 10 and 55 dB SPL. At 1.5 kHz, DPEs were essentially nonexistent. Thus, the observed asymmetry in the frequency extent of DPE I/O activity supported the asymmetry noted in the hearing for the two ears, around 1–2 kHz. By 6 kHz, (FIG. 7F) the behavioral measures (FIG. 7A) indicate that the right ear has slightly better hearing than the left. Similarly, the DPE I/O curves for 6 kHz (FIG. 7F) support the behavioral observation in that the detection "thresholds" for the left ear are about 5 dB poorer than the comparable measures for the right ear. In general, DPEs track hearing loss due to noise exposure accurately. This is believed to be so because excessive sound injures the outer hair cells preferentially, especially in the beginning stages. It is believed that DPEs selectively test outer hair-cell functioning.

Returning to FIG. 5, both DPE audiograms and I/O functions may be graphically displayed by means of a plotter 68 under control of digital computer 50. The plotter used in the laboratory embodiment of the invention was an HP 7470A plotter, but of course, a wide variety of commercial plotters could be used as would be known to one of ordinary skill in the data processing art. Likewise printer 70, under control of computer 50 serves to provide a print-out of DPE audiograms or I/O functions. Such DPE audiograms or I/O functions may also advantageously be displayed on a CRT or the like (not illustrated).

Figure 8A:
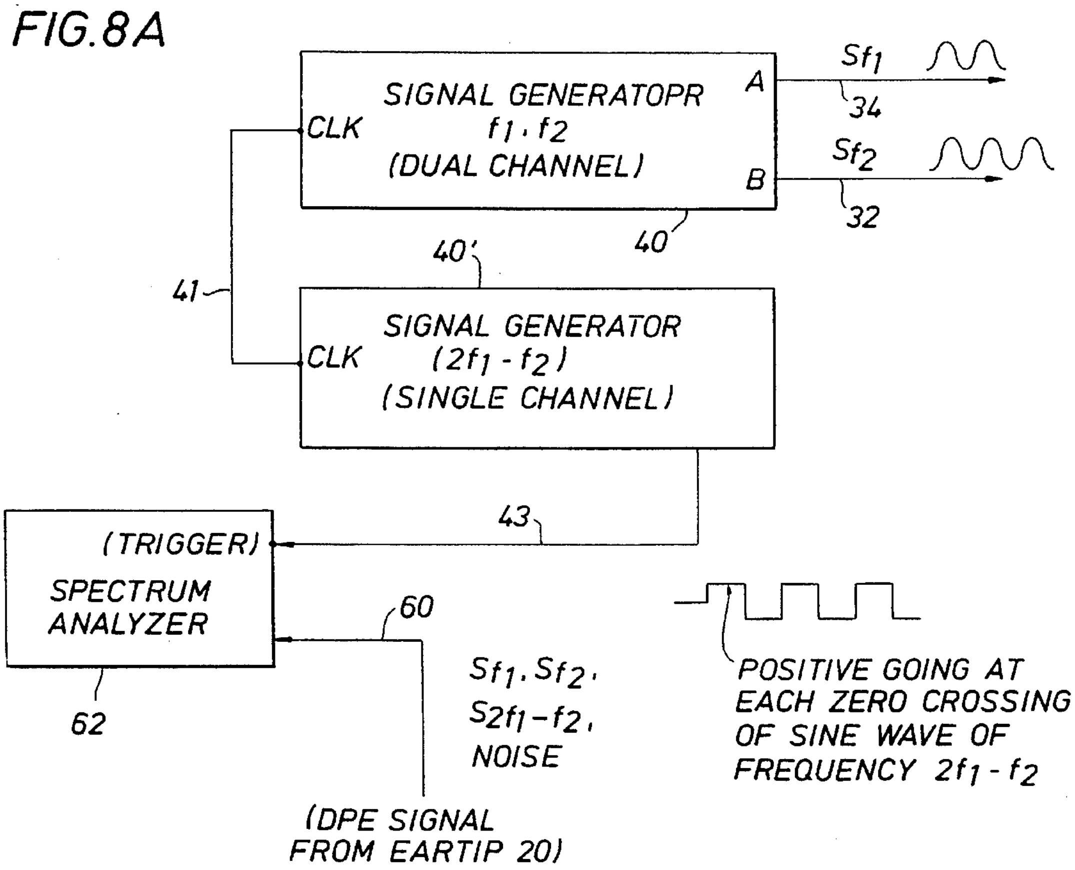
FIGS. 8A and 8B illustrate two embodiments of the phase-locked averaging feature of the invention by which the noise floor of the DPE signal is reduced.

Turning now to FIG. 8A, an illustration of the phase-locked averaging of the DPE signals is shown which is performed in order to reduce the noise level or "floor" shown at FIG. 6A. A signal generator 40 as shown in FIG. 5 is provided to generate signals $S_{f1}$ and $S_{f2}$ on leads 32, 34. The master clock of signal generator 40 (Hewlett Packard 3326A) is connected to the master clock of single channel signal generator 40'. Signal generator 40' is set to the DPE frequency $2f_1-f_2$. Connection of the master clocks of signal generators 40 and 40' insures that there is no phase drift among any of the three signals, i.e., $S_{f1}$, $S_{f2}$, $S_{2f1-f2}$, because all clocks are synchronized.

Signal generator 40' produces a square wave output on lead 43 such that its positive going pulse is synchronized with the positive going sine wave of frequency $2f_1-f_2$. Such square wave of frequency $2f_1-f_2$ is applied to the trigger input of spectrum analyzer 62. A time average is determined by real-time spectrum analyzer 62 each time it is triggered by the positive going zero crossing signal on lead 43. Accordingly, the time average of the DPE signal is initiated for each sample of the DPE signal at the same phase of such DPE signal. Such procedure assures that all of the DPE signal is added to the averaged waveform, but noise signals of different frequencies than that of the DPE signal will be out of phase from sample to sample. Accordingly, the noise signal, dissimilar in phase, is substantially reduced during the averaging process.

Once the time averaged waveform has been collected, spectrum analyzer 62 uses standard Fourier-transform techniques to determine the level of the DPE signal, and of course the noise floor for frequencies other than that of the DPE signal. Using the method and apparatus of FIG. 8A to augment that of FIG. 5, background noise is reduced by approximately 15 dB below that observed without the phase-locking method and apparatus.

Figure 8B:
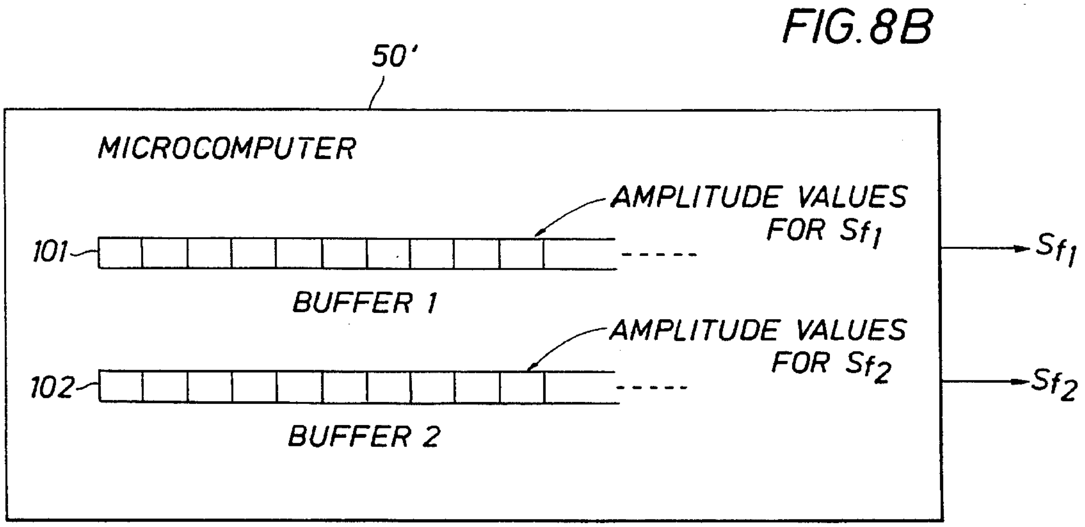

The phase-locking feature of the invention described above provides a means for repeatedly initiating a time sample at the same phase of the DPE signal. An alternative method for accomplishing such phase-locking is illustrated in FIG. 8B. Rather than using a stand-alone signal generator 40, signals $S_{f1}$ and $S_{f2}$ are generated by microcomputer 50. Two wave form buffers are established in the memory of computer 50'. The buffers 101,102 store the digitized time values for $S_{f1}$ and $S_{f2}$.

Each buffer is set to an integer multiple of the length of the DPE period. After output of each point in the buffer, exactly one period of an integer multiple of the period of the DPE signal has elapsed. For example, if a buffer contains 1,000 points for an output signal, representing 1 microsecond per point, such buffer is equivalent to a DPE frequency of 1 kHz each time the information in the buffer is completed.

Another alternative approach, one not involving computer generation of the primary-tone signals, provides a computer clock running at the period of the DPE frequency. For example, if the clock is set to "tick" once per microsecond, 1,000 ticks would be equivalent to 1 millisecond, i.e., the period of a 1-kHz DPE. At the end of every 1,000 ticks, an interrupt would be generated to instruct the computer to initiate another time sample. If the time sample is longer than one period of the distortion-product frequency, the computer would simply wait until the next 1,000 ticks have elapsed. With the clock running continuously, the phase of the distortion product would be constant from sample to sample.

FIG. 9 illustrates still another apparatus and method for reducing noise when measuring DPE signals. A significant amount of body noise is created by the patient during the measurement. Coughing, sneezing and other body noises contaminate the DPE signal. FIG. 9 shows that two microphones 30A, 30B are placed in ear canal 16 to pick up the DPE signal. The output of one microphone 30A is applied via lead 120 to the plus input of differential amplifier 130. The output of a second less sensitive microphone 30B is applied via lead 122 through variable gain amplifier and phase shifter circuits 124, 126 via lead 128 to the minus input of differential amplifier 130. The output of microphone 30B is of less sensitivity so that the frequency component of $S_{2f1-f2}$ (the DPE signal) is missing from the signal applied to the minus input of differential amplifier. The gain and phase of this signal via lead 128 are then adjusted to yeild maximum cancellation when applied to differential amplifier 130. That part of the lower frequency signal appearing on lead 128 due to the bodily noise is relatively unchanged. As a result, the output of differential amplifier 130 produces on lead 132 a signal comprising the DPE signal, with the body noise signal greatly reduced.

Various modifications and alterations in the described methods and apparatus will be apparent to those skilled in the art of the foregoing description which does not depart from the spirit of the invention. For this reason, these changes are desired to be included in the appended claims. The appended claims recite the only limitation to the present invention. The descriptive manner which is employed for setting forth the embodiments is to be interpreted as illustrative but not limitative.

APPENDIX A

```
      MAIN PROGRAM DPOAE
C
C     BYTES
C
      BYTE  PTB(20),RIT(20),DSPF(10)
      BYTE  IDATE(9),SETNAM(6),OLDSET(6),CTLFIL(11),RTYPE
      BYTE  XFRFIL(16),GRFILE(11),CORFIL(11),SJT,AFT,NFR,PRSW,GRD
C
C     DIMENSIONS
C
      DIMENSION  CFRO(4),DBO(4),DPO(4),RNO(4)
C
C     COMMONS
C
      COMMON /COM001/ CORFIL,GRFILE,XFRFIL,RTYPE,NFR,PRSW,GRD,SJT,AFT
      COMMON /COM002/ ILOG,LR,IYA,XLO,YLO,XHI,YHI,AX,XLN,XSCALE,YLN,YSCALE
      COMMON /COM003/ DPKHZ,FAKHZ,FAATTN,FBKHZ,FBATTN,DBSPL,STZ,STP,TDB
      COMMON /COM004/ CFRO,DBO,DPO,RNO
      COMMON /COM005/ XINC,XLBINC,YINC,YLBINC
      COMMON /COM006/ RNOISE,DPAMP
      COMMON /COM009/ IPTB,IRIT,PTB,RIT
      COMMON /COM010/ SETNAM,OLDSET
C
C     DATA
C
      DATA LR      /55/        !GRAPH EDGE REF., 55 X AND 55 Y
      DATA NBRAVG  /4/
      DATA CRIT    /5.0/
      DATA VN      /1.07/
      DATA SPAN    /10.0/
C
      DATA SETNAM  /6*' '/
      DATA OLDSET  /6*' '/
      DATA  CORFIL,GRFILE /11*' ',11*' '/
      DATA  XFRFIL  /'D','I','G',':',12*'  '/
      DATA  RTYPE,PRSW,NFR,GRD,SJT,AFT /'I','Y','Y','Y','R','N'/
C
C      ***************************************************************
C     PROGRAM STARTS
C
5     CALL SCFUNC(1,N,N)
      CALL SCFUNC(3,1,1)
      WRITE  (5,10)  VN
1 0   FORMAT(1X,'                       DISTORTION PRODUCT'/1X,
   + '           OTOACOUSTIC EMISSION COLLECTION PROGRAM'/1X,
    + '                        VN.  ',F5.2)
C
      CALL DATE(IDATE)
      IF (IDATE(1) .EQ. ' ') STOP 'ENTER DATE THEN RE-RUN PROGRAM'
C
      J  =  IBUP(2,0)          !CLEAR ALL DEVICES
```

```
      J = IBUP(10)         !FINISH
C
C Set synthesizer to safe levels and tones
C
      CALL HPCHAN ('B')
      CALL HPATTN (80.0)
      CALL HPFREQ (30.0)
      CALL HPCHAN ('A')
      CALL HPATTN (80.0)
      CALL HPFREQ (30.0)
C
380   CALL SCFUNC(3,6,1)
      WRITE (5,400) 27
400   FORMAT(1X,1A1,'[0J','ENTER CONTROL FILE: ',$)
C
      READ (5,600) CTLFIL
600   FORMAT(11A1)
C
      CALL FILXST(IX,CTLFIL)
      IF (IX .GT. 0) GO TO 800
C
      CALL TEKOUT(7)
      GO TO 380
C
C     READ CONTROL FILE DATA
C
800   CALL ASSIGN(2,CTLFIL)
      CALL RDCNFL(1,IERR,NBRAVG,SPAN,CRIT)
C
      IGP = 1
      CALL FILXST(IX,GRFILE)
      IF (IX .GT. 0) GO TO 900
      IGP = 0
      CALL INSERT('NONE       ',GRFILE,1,11)
C
900   ICOR = 1
      CALL FILXST(IX,CORFIL)
      IF (IX .GT. 0) GO TO 1000
      ICOR = 0
      CALL INSERT('NONE       ',CORFIL,1,11)
C
1000  CALL DPPPRM(NTYPE,CRIT,NBRAVG,SPAN,STP,IGP,ICOR)
C
      NTYPE = 0                    !DEFAULT TO I/O
      IF (RTYPE .EQ. 'A') NTYPE = 1     !ELSE, AUDIOGRAM
      IF (RTYPE .EQ. 'R') NTYPE = 2     !OR RATIO
C
      CALL MACTIT(XFRFIL,DSPF,RTYPE,SJT)
C
      WRITE (5,1100) 27,7
1100  FORMAT(1X,1A1,'[97a^!6C^!6Q\',1A1)
```

```
C
      IF (NTYPE) GO TO 1150
      CALL DPIOEX(NTYPE,ICOR,IGP,NBRAVG,SPAN,CRIT,CTLFIL,DSPF)
      GO TO 1200
C
1150  CALL DPAREX(NTYPE,ICOR,IGP,NBRAVG,SPAN,CRIT,DSPF)
C
1200  IF (AFT .NE. 'Y') GO TO 5
C
      WRITE(5,1210)27,XFRFIL
1210  FORMAT(1X,1A1,'[97a\.^C',
   +  'R KERM11^M\>SEND ',16A1)
C
      WRITE (5,1220) 7
1220  FORMAT(1X,'^M^#1N\>^C\.R DPOAE^M\',1A1)
C
      END
XXXXXXXXXXXXXXXXXXXXXXXXXXXXXXXXXXXXXXXXXXXXXXXXXXXXXXXXXXXXX
```

BEGINNING OF SUBROUTINES IN ALPHABETICAL ORDER

```
      SUBROUTINE  CFRKHZ(ICOR,XFRFIL,CTLFIL,CORFIL,WRBF)
C
      BYTE  CFRFIL(16),CTLFIL(11),CORFIL(11),WRBF(150),TSTB(6)
C
C
*****************************************************************
C     SUBR STARTS
C
      IP = 1
C
      DO 100 I = 1,150
      WRBF(I) = ' '
100   CONTINUE
C
      IF (.NOT. (ICOR)) GO TO 1000
      CALL ASSIGN(3,CORFIL)
C
200   READ (3,300) CFR,X
300   FORMAT(2F9.3)
C
      IF (CFR .EQ. 999.0) GO TO 500
      IF (IP .GT. 1) WRBF(IP-1) = 9
      ENCODE (6,400,WRBF(IP)) CFR
400   FORMAT(F6.3)
C
      IP = IP + 7
      GO TO 200
C
500   IP = IP - 2
```

```
      REWIND 3
C
      GO TO 2000
C
1000  REWIND 2
C
      DO 1200 I = 1,5
      READ (2,1100) TSTB
1100  FORMAT(6A1)
1200  CONTINUE
C
1300  READ (2,1400,ERR=1500) TSTB,CFR
1400  FORMAT (2X,6A1,2X,F7.3)
C
      IF (TSTB(1) .EQ. 'S') GO TO 1300
      IF (TSTB(1) .EQ. '_') GO TO 1500
C
      IF (IP .GT. 1) WRBF(IP-1) = 9
      ENCODE (6,400,WRBF(IP)) CFR
C
      IP = IP + 7
      GO TO 1300
C
1500  IP = IP - 2
      REWIND 2
C
      DO 1600 I = 1,5
      READ (2,1100) TSTB
1600  CONTINUE
C
2000  WRITE (1,2100) (WRBF(J),J=1,IP)
2100  FORMAT(150A1)
C
      RETURN
      END

      SUBROUTINE DPAREX(NTYPE,ICOR,IGP,NBRAVG,SPAN,CRIT,PFIL)
C
C     BYTES
C
      BYTE PTB(20),RIT(20)
      BYTE PFIL(10),WRBF(150),EB
      BYTE IDATE(9),SETNAM(6),OLDSET(6),RTYPE
      BYTE XFRFIL(16),GRFILE(11),CORFIL(11),SJT,AFT,NFR,PRSW,GRD
C
C     DIMENSIONS
C
      DIMENSION CFRO(4),DBO(4),DPO(4),RNO(4),TNS(50)
C
C     COMMONS
C
```

```
      COMMON /COM001/ CORFIL,GRFILE,XFRFIL,RTYPE,NFR,PRSW,GRD,SJT,AFT
      COMMON /COM002/ ILOG,LR,IYA,XLO,YLO,XHI,YHI,AX,XLN,XSCALE,YLN,YSCALE
      COMMON /COM003/ DPKHZ,FAKHZ,FAATTN,FBKHZ,FBATTN,DBSPL,STZ,STP,TDB
      COMMON /COM004/ CFRO,DBO,DPO,RNO
      COMMON /COM006/ RNOISE,DPAMP
      COMMON /COM009/ IPTB,IRIT,PTB,RIT
      COMMON /COM010/ SETNAM,OLDSET
C
C
C
*************************************************************
*******
C     SUBR. STARTS
C
C     PLOT X/Y AXIS, TICS, & LABELS
C
      IF (.NOT. (IGP)) GO TO 5
      CALL DPARP(NTYPE)
      CALL TCPPLT(1,450,460)          !PUT FILE NAME ON GRAPH
      WRITE (5,3300) 31,PFIL
      CALL TCPPLT(1,450,445)
      WRITE (5,3310) 31,(PTB(J),J=1,IPTB)
      CALL TCPPLT(1,450,430)
      WRITE (5,3310) 31,(RIT(J),J=1,IRIT)
C
5     EB = 'E'
      IEOF = 0
      CALL SCCA(ICC)
      CALL IPOKE("44, IPEEK("44) .OR. "050100)
C
10    KEY = ITTINR()               !FLUSH ANY PREV. KEYS
      IF (KEY .GE. 0) GO TO 10
C
C
      IF (PRSW .EQ. 'Y') CALL DPPRNT(1,NTYPE,CFR,DBSPL,DPAMP,RNOISE,PFIL)
      IF (.NOT. (ICOR)) GO TO 150     !SKIP IF NO CORREC. FILE
      CALL ASSIGN (3,CORFIL)          !ELSE, OPEN IT
C
150   IPASS = 0
C
200   IW = 1                       !WRITE POINTER = 1
      IF (PRSW .NE. 'Y') GO TO 220
      IF (.NOT. (IPASS)) CALL DPPRNT(2,NTYPE,CFR,DBSPL,DPAMP,RNOISE,PFIL)
C
220   CALL RDCNFL(2,IEOF,NBRAVG,SPAN,CRIT) !READ CONTROL DATA
      IF (IEOF) GO TO 2000              !OUT, IF EOF
      DBSPLM = DBSPL                    !SAVE ORIG. dB
      STEP  = STZ                       !SAVE dB STEP SIZE
C
      ILC = INT((DBSPL - TDB) / STZ) + 1  !CALC. NUMBER OF LOOPS
      IF (IPASS) GO TO 300
```

```
C
      IP = 1
      DX = DBSPL
      DO 250 I = 1,ILC
      ENCODE (3,230,WRBF(IP)) INT(DX)
230   FORMAT(I3)
C
      DX = DX - STZ
      IP = IP + 4
      WRBF(IP-1) = 9
250   CONTINUE
C
      IP = IP - 2
      WRITE (1,260) (WRBF(J),J=1,IP)
260   FORMAT(150A1)
C
C Set analyzer to set-up for this run.
C
300   CALL SNDSET(NBRAVG,SPAN)
C
      CDB = 0.0                    !DB CORRECTION = 0 dB
      IF (ICOR) READ (3,310) CFR,CDB     !READ CORRECTION FACTORS
310   FORMAT(2F9.3)
C
      IWF = 0
      DO 1000 I = 1,ILC       !NO. OF DP MEASUREMENTS LOOP
      KEY = ITTINR()              !READ KEYBOARD
      IF (KEY .EQ. 3) GO TO 2000     !LEAVE LOOP IF INPUT
      ISV = I               !SAVE FILE NUMBER POINTER
C
C Set synthesizer frequency, attenuation
C
      CALL NSFLRJ(TNS(ISV),CRIT,CDB,IPASS,NFR)
C
C     IF NO CORRECTION FACTORS, FREQ. = DPKHZ, CDB = 0.0.
C     FOR RATIO TYPE, FREQ = RATIO OF B / A
C
      IF (.NOT. (ICOR)) CFR = DPKHZ
      IF (NTYPE .EQ. 2) CFR = FBKHZ / FAKHZ
C
      CALL DPDSPD(IGP,NTYPE,IPASS,CFR,DPAMP,RNOISE,DBSPL,ISV,PFIL)
      IF (PRSW .EQ. 'Y') CALL DPPRNT(5,NTYPE,CFR,DBSPL,DPAMP,RNOISE,PFIL)
C
C     Write out the DPamp value, paired with DPKHZ
C
      IF (IWF) GO TO 700
      ENCODE (7,650,WRBF(IW)) CFR
650   FORMAT(F7.3)
C
      IWF = 1
      IW = IW + 8
```

```
      WRBF(IW-1) = 9
C
700   ENCODE (7,650,WRBF(IW)) DPAMP
      IW = IW + 8
      WRBF(IW-1) = 9
      ENCODE (7,650,WRBF(IW)) RNOISE
      IW = IW + 8
      WRBF(IW-1) = 9
C
C Calculate next attenuation, applying DB step size. Ensure also that
C dBattn has not reached max and that DPamp is still above the noise level.
C
      FAattn = FAattn + STZ
      IF (FAATTN .GT. 80.0) GO TO 1100
      FBattn = FBattn + STZ
      IF (FBATTN .GT. 80.0) GO TO 1100
      dBSPL = dBSPL - STZ
C
1000  CONTINUE
C
1100  IPASS = 1            !AT LEAST 1 PASS COMPLETED
      IW = IW - 2
      WRITE (1,260) (WRBF(J),J=1,IW)
C
      GO TO 200        !NEXT GROUP IF NOT DOUBLE CTRL/C
C
2000  CALL HPCHAN ('B')        !MAX VALUES TO SYNTHESIZER
      CALL HPATTN (80.0)
      CALL HPFREQ (30.0)
      CALL HPCHAN ('A')
      CALL HPATTN (80.0)
      CALL HPFREQ (30.0)
      KSV = KEY
C
      WRITE (1,3020) EB
3020  FORMAT(1A1/)
C
      CALL CLOSE (1)
      CALL CLOSE (2)
      IF (ICOR) CALL CLOSE(3)
      IF (IGP) CALL CLOSE (4)
      CALL IPOKE("44,IPEEK("44) .AND. (.NOT. "050100))
3010  KEY = ITTINR()            !FLUSH ANY PREV. KEYS
      IF (KEY .GE. 0) GO TO 3010
      CALL SCCA
C
      IF (KSV .NE. 3) GO TO 3060
      IF (AFT .NE. 'Y') GO TO 6000
C
      WRITE (5,3050) 24
3050  FORMAT(/$1X,1A1,'FILE TRANSFER TO MAC AS SELECTED? [N/Y]: ')
```

```
C
        READ (5,3100) AFT
C
        GO TO 6000
C
3060    IF (.NOT. (IGP)) GO TO 6000  !SKIP IF NOT IN GRAPH MODE
        IF (GRD .EQ. 'N') GO TO 6000 !SKIP IF NO DUMP TO PRINTER
C
        CALL ASSIGN (1,XFRFIL)
        READ (1,3100)  WRBF(1)
        READ (1,3100)  WRBF(1)
        READ (1,3100)  WRBF(1)
        READ (1,3100)  WRBF(1)
        READ (1,3100)  WRBF(1)
        READ (1,3100)  WRBF(1)
3100    FORMAT(1A1)
C
C       SEND GRAPH TO PRINTER
C
        CALL DPARP(NTYPE)
        CALL DATE(IDATE)
C
        CALL TCPPLT(1,450,450)       !PUT DATE ON GRAPH
        WRITE (5,3200) 31,IDATE
3200    FORMAT(1X,1A1,9A1,$)
C
        CALL TCPPLT(1,450,430)       !PUT FILE NAME ON GRAPH
        WRITE (5,3300) 31,PFIL
3300    FORMAT(1X,1A1,10A1)
C
        CALL TCPPLT(1,450,410)
        WRITE (5,3310) 31,(PTB(J),J=1,IPTB)
3310    FORMAT(1X,1A1,20A1)
        CALL TCPPLT(1,450,390)
        WRITE (5,3310) 31,(RIT(J),J=1,IRIT)
C
        IPASS = 0
C
3500    READ (1,3600,END=5100) N,WRBF
3600    FORMAT(Q,150A1)
C
        IF (WRBF(1) .EQ. 'E') GO TO 5100
        DECODE (7,650,WRBF(1)) CFR
        IW = 9
C
        DBSPL = DBSPLM
C
        DO 5000 I = 1,3
        ISV = I
        IYA = ((I * 150) - 150) + 40    !Y ADJUSTER
C
```

```
      DECODE (7,650,WRBF(IW),ERR=5000) DPAMP
      IF (DPAMP .EQ. 0.0) GO TO 5000
      IW = IW + 8
      DECODE (7,650,WRBF(IW)) RNOISE
      IW = IW + 8
C
      CALL DPARPL(1,CFR,DBSPL,DPAMP,RNOISE,IPASS,ISV)
C
      IF (IPASS) GO TO 5000
      IY = ((I * 150) - 150) + 40     !Y OFFSET FOR FILES 1 TO 3
      CALL TCPPLT(1,375,IY)
      WRITE (5,4010) 31,INT(DBSPL)
4010  FORMAT(1X,1A1,'LEVEL ',I3,' dB SPL')
C
      DBSPL = DBSPL - STEP
C
5000  CONTINUE
C
      IPASS = 1
      GO TO 3500
C
5100  CALL CLOSE (1)
      CALL CLOSE (4)
C
      WRITE (5,5200) 27,23
5200  FORMAT(1X,2A1)
C
6000  CALL TEKOUT(24)
C
      RETURN
      END
      SUBROUTINE DPARP(NTYPE)
C
      BYTE CORFIL(11),GRFILE(11)
C
      COMMON /COM001/ CORFIL,GRFILE
      COMMON /COM002/ ILOG,LR,IYA
C
C
*******************************************************************
***
C     SUBR. STARTS
C
      CALL GPFPRM(NTYPE,GRFILE)     !READ GRAPH PARAMS
C
      ITITLE = 1
      IFRL = 1
      DO 20 I = 1,3               !3 PLOT LOOP
C
      IYA = ((I * 150) - 150) + 40    !Y ADJUSTER
      CALL DPPLT1(NTYPE,ITITLE,IFRL)    !SET UP GRAPH
```

```
      ITITLE = 0
      IFRL = 0
C
20    CONTINUE
C
C     PLOT AVG. +/- ST.DEV DATA
C
      WRITE (5,30) 27,97        !MAKE DOTTED LINES
30    FORMAT(1X,2A1,$)
C
      DO 100 I = 1,3            !3 PLOT LOOP
      IYA = ((I * 150) - 150) + 40   !Y ADJUST
C
      DO 50 J = 1,4             !4 ST.DEV LINES
      IBP = 1         !IBP POINTS TO CHAR 29 (GS) TO INIT PLOT
      CALL DPPLT2(IBP,IPERR)    !PLOT LINES
      IF (IPERR) GO TO 110      !110 = EOF
50    CONTINUE
C
100   CONTINUE              !3 PLOT LOOP TARGET
C
110   CALL CLOSE (3)        !CLOSE FILE
C
      WRITE (5,30) 27,96     !RETURN TO SOLID LINES
C
      RETURN
      END
      SUBROUTINE  DPARPL(ISKW,CFR,DBSPL,DPAMP,RNOISE,IPASS,ISV)
C
      DIMENSION  CFRO(4),DBO(4),DPO(4),RNO(4)
C
      COMMON /COM002/ ILOG,LR,IYA,XLO,YLO,XHI,YHI,AX,XLN,XSCALE,YLN,YSCALE
      COMMON /COM004/ CFRO,DBO,DPO,RNO
C
C
*****************************************************************
*****
C     SUBR. STARTS
C
      IP = ISV                 !TEXT POINTER = FILE NO.
      IY = ISV                 !Y POINTER = FILE NO.
      IX = 375                   !MAX X = 325
      IF (IY .GT. 3) IY = 3     !DISPLAY NO MORE THAN 3 GRAPHS
      IF (IP .GT. 4) IP = 4     !NO MORE THEN 4 INFO. GROUPS
      IY = ((IY * 150) - 150) + 40   !Y OFFSET FOR FILES 1 TO 3
      IF (IP .GT. 3) IY = 415     !Y OFFSET FOR BEYOND 3RD FILE
C
      IF (ISKW) GO TO 600    !SKIP IF PLOT DATA, NOT TEXT
C
      WRITE (5,200) 31,27,127 !ERASE SEQ. FOR MAC
200   FORMAT(1X,3A1,$)
```

```
C
      CALL TCPPLT(1,IX,IY)        !ERASE PREV. TEXT
      WRITE (5,300) 31,CFRO(IP),DBO(IP),DPO(IP),RNO(IP) !REWRITE = ERASE
300   FORMAT (1X,1A1,4(' ',F7.3))
C
      CALL TEKOUT(13)
C
      CALL TCPPLT(1,IX,IY) !DISPLAY CURRENT DATA
      WRITE (5,300) 31,CFR,DBSPL,DPAMP,RNOISE
C
600   IBP = 1
      IF (IPASS) IBP = 2
C
      IYA = IY
      IF (IP .GT. 3) GO TO 1000
      IF (IPASS) CALL PLTLIN(1,1,IX,IY,1,CFRO(IP),DPO(IP))
      CALL PLTLIN(1,1,IX,IY,IBP,CFR,DPAMP)
      CALL PLTCRS(IX,IY,2)
      IF (IPASS) CALL PLTLIN(1,1,IX,IY,1,CFRO(IP),RNO(IP))
      CALL PLTLIN(1,1,IX,IY,IBP,CFR,RNOISE)
C
1000  CFRO(IP) = CFR              !UPDATE AS PREV. INFO
      DBO(IP) = DBSPL
      DPO(IP) = DPAMP
      RNO(IP) = RNOISE
C
      RETURN
      END
      SUBROUTINE  DPCDFX(IFN,FIL)
C
      BYTE FIL(16)
C
C
*******************************************************************
******
C     SUBR STARTS
C
      IP = (INDEX(FIL,'.')) + 1
      ENCODE (3,3150,FIL(IP)) IFN     !ENCODE FILE # AS FILE EXTENSION
3150  FORMAT(I3)
C
      IF (FIL(IP) .EQ. ' ') FIL(IP) = '0'     !REPLACE WITH ZERO IF SPACE
      IF (FIL(IP+1) .EQ. ' ') FIL(IP+1) = '0' !REPLACE WITH ZERO IF SPACE
      FIL(IP+3) = 0
C
      RETURN
      END
      SUBROUTINE
DPDSPD(IGP,NTYPE,IPASS,CFR,DPAMP,RNOISE,DBSPL,ISV,PFIL)
C
      BYTE PFIL(10)
```

```
C
C
*****************************************************************
*******
C      SUBR. STARTS
C
       IF (IGP) GO TO 530        !SKIP IF GRAPH MODE
C
       WRITE (5,510) CFR,DBSPL,DPAMP,RNOISE,PFIL
510    FORMAT  (/1X,4('  ',F7.3),'    ',10A1)
       RETURN
C
530    IF (NTYPE) GO TO 700
C
       CALL DPIOPL(0,CFR,DBSPL,DPAMP,RNOISE,IPASS)
       RETURN
C
700    CALL DPARPL(0,CFR,DBSPL,DPAMP,RNOISE,IPASS,ISV)
C
       RETURN
       END
       SUBROUTINE  DPIOEX(NTYPE,ICOR,IGP,NBRAVG,SPAN,CRIT,CTLFIL,PFIL)
C
       BYTE  PTB(20),RIT(20)
       BYTE  WRBF(150),PFIL(10),WDAT(19),EB
       BYTE  IDATE(9),SETNAM(6),OLDSET(6),CTLFIL(11)
       BYTE  CORFIL(11),GRFILE(11),XFRFIL(16),RTYPE,NFR,PRSW,GRD,SJT,AFT
C
       DIMENSION CFRB(50)
       DIMENSION  CFRO(4),DBO(4),DPO(4),RNO(4)
C
       COMMON /COM001/ CORFIL,GRFILE,XFRFIL,RTYPE,NFR,PRSW,GRD,SJT,AFT
       COMMON /COM002/ ILOG,LR,IYA,XLO,YLO,XHI,YHI,AX,XLN,XSCALE,YLN,YSCALE
       COMMON /COM003/ DPKHZ,FAKHZ,FAATTN,FBKHZ,FBATTN,DBSPL,STZ,STP,TDB
       COMMON /COM004/ CFRO,DBO,DPO,RNO
       COMMON /COM006/ RNOISE,DPAMP
       COMMON /COM009/ IPTB,IRIT,PTB,RIT
       COMMON /COM010/ SETNAM,OLDSET
C
C
*****************************************************************
*******
C      SUBR. STARTS
C
C      GO GET CORRECTION FACTOR DATA OR DPKHZ DATA TO WRITE AS A LINE
C      INTO XFR FILE.
C
       IYA = 40      !Y ADJUST FOR PLOT
       IEOF = 0      !CLEAR END OF FILE FOR CONTROL FILE
       ISK = 1       !NO LINE SKIP FOR 1ST SET OF DATA
       EB = 'E'
```

```
      LENTST = 0
C
      CALL CFRKHZ(ICOR,XFRFIL,CTLFIL,CORFIL,WRBF)
C
      IF (PRSW .EQ. 'Y') CALL DPPRNT(1,NTYPE,CFR,DBSPL,DPAMP,RNOISE,PFIL)
      IF (IGP) CALL GPFPRM(NTYPE,GRFILE) !READ GRAPH PARAMS
C
      ICC = 0                    !^C FLAG
      CALL SCCA(ICC)
      CALL IPOKE("44, IPEEK("44) .OR. "050100)
C
10    KEY = ITTINR()             !FLUSH ANY PREV. KEYS
      IF (KEY .GE. 0) GO TO 10
C
C
*********************************************************************
**
C     TARGET FOR DP MAIN LOOP
C
100   CDB = 0.0                  !PRE-SET dB CORRECTION TO 0.0
C
      IF (ICOR) READ (3,150,END=3000) CFR,CDB     !READ CORRECTION FACTORS
150   FORMAT(2F9.3)
C
      CALL RDCNFL(2,IEOF,NBRAVG,SPAN,CRIT) !READ CONTROL DATA
      IF (IEOF) GO TO 3000            !OUT, IF EOF
      IF (.NOT. (LENLN)) WRITE (1,160) INT(DBSPL),9,INT(STZ),9,INT(TDB)
160   FORMAT(I3,1A1,I3,1A1,I3)
      LENLN = 1
C
      IF (.NOT. (ICOR)) CFR = DPKHZ   ! CFR = VAL. FROM COR FILE OR DPKHZ
      IF (PRSW .EQ. 'Y') CALL DPPRNT(3,NTYPE,CFR,DBSPL,DPAMP,RNOISE,PFIL)
      IF (.NOT. (IGP)) GO TO 300      !SKIP IF NO GRAPH PARAM. FILE
C
C     MAKE PLOT AXIS, TICS, LABELS, ETC.
C
      CALL DPIOP(NTYPE)
      CALL TCPPLT(1,450,300)
      WRITE (5,200) 31,PFIL
200   FORMAT(1X,10A1,$)
      CALL TCPPLT(1,450,240)
      WRITE (5,3670) 31,(PTB(J),J=1,IPTB)
      CALL TCPPLT(1,450,220)
      WRITE (5,3670) 31,(RIT(J),J=1,IRIT)
C
C Set analyzer to set-up for this run.
C
300   CALL SNDSET(NBRAVG,SPAN)        !SIGNAL ANAL. SETUP
C
      IPASS = 0                       !CLEAR PASSES
      LOOPN = INT((DBSPL - TDB) / STZ) + 1  !CALC. LOOP STEPS
```

```
C
      DO 1000 I = 1,LOOPN      !LOOP THRU dB STEPS
      KEY = ITTINR()            !READ KEYBOARD
      IF (KEY .EQ. 3) GO TO 2000    !LEAVE LOOP IF ^C
C
C     GET DPAMP, RNOISE, CHECK NOISE FLOOR REJECTION.
C     GRAPH AND OR DISPLAY DATA.
C
      CALL NSFLRJ(TN,CRIT,CDB,IPASS,NFR)
      CALL DPDSPD(IGP,NTYPE,IPASS,CFR,DPAMP,RNOISE,DBSPL,ISV,PFIL)
C
      IF (PRSW .EQ. 'Y') CALL DPPRNT(4,NTYPE,CFR,DBSPL,DPAMP,RNOISE,PFIL)
C
      IPASS = 1                 !PASS COMPLETED
C
C     Write out the DPAMP value, paired with DPKHZ
C
      CALL INSERT('                   ',WDAT,1,19)
      ENCODE (3,650,WDAT(1)) INT(DBSPL)
650   FORMAT(I3)
C
      WDAT(4) = 9
      ENCODE (7,700,WDAT(5)) DPAMP
      WDAT(12) = 9
      ENCODE (7,700,WDAT(13)) RNOISE
700   FORMAT(F7.3)
C
C
      IF (ISK) WRITE (1,750) WDAT
      IF (.NOT. (ISK)) WRITE (1,755) EB,WDAT
750   FORMAT(19A1)
755   FORMAT(1A1/19A1)
      ISK = 1
C
C Calculate next attenuation, applying DB step size. Ensure also that
C dBattn has not reached max and that DPAMP is still above the noise level.
C
      IF (STP .EQ. 0.0) GO TO 800
C
      IF (DPAMP .LT. (RNOISE + STP)) GO TO 2000  !BASE LIMIT CHECK
C
800   FAATTN = FAATTN + STZ             !ADJUST FOR NEXT PASS
      IF (FAATTN .GT. 80.0) GO TO 2000
      FBATTN = FBATTN + STZ
      IF (FBATTN .GT. 80.0) GO TO 2000
      DBSPL = DBSPL - STZ
C
1000  CONTINUE
C
2000  CALL HPCHAN ('B')          ! ^C^C OR STEP LOOP TARGET
      CALL HPATTN (80.0)
```

```
      CALL HPFREQ (30.0)
      CALL HPCHAN ('A')
      CALL HPATTN (80.0)
      CALL HPFREQ (30.0)
      KSV = KEY
C
      IF (IGP) WRITE (5,2100) 27,12        !ERASE GRAPH SCREEN
2100  FORMAT(1X,2A1)
C
      ISK = 0
      IF (KSV .NE. 3) GO TO 100
C
3000  CALL HPCHAN ('B')          ! END OF FILE/TEST TARGET
      CALL HPATTN (80.0)
      CALL HPFREQ (30.0)
      CALL HPCHAN ('A')
      CALL HPATTN (80.0)
      CALL HPFREQ (30.0)
C
      WRITE (1,3020) EB
3020  FORMAT(1A1/)
C
      CALL CLOSE (1)
      CALL CLOSE (2)
      IF (ICOR) CALL CLOSE(3)
      IF (IGP) CALL CLOSE (4)
3010  KEY = ITTINR()              !FLUSH ANY PREV. KEYS
      IF (KEY .GE. 0) GO TO 3010
      CALL IPOKE("44,IPEEK("44) .AND. (.NOT. "050100))
      CALLSCCA
C
      IF (KSV .NE. 3) GO TO 3160
      IF (AFT .NE. 'Y') GO TO 5100
C
      WRITE (5,3050) 24
3050  FORMAT(/$1X,1A1,'DO FILE TRANSFER TO MAC AS SELECTED? [N/Y]: ')
C
      READ (5,3100) AFT
3100  FORMAT(1A1)
C
      GO TO 5100
C
3160  IF (.NOT. (IGP)) GO TO 5100
      IF (GRD .EQ. 'N') GO TO 5100
C
      CALL DATE(IDATE)
      CALL GPFPRM(NTYPE,GRFILE)
      CALL ASSIGN(1,XFRFIL)
      READ (1,3100) WDAT(1)       !READ PAST INITIAL FILE INFO
      READ (1,3100) WDAT(1)
      READ (1,3100) WDAT(1)
```

```
      READ  (1,3100)  WDAT(1)
      READ  (1,3100)  WDAT(1)
      READ (1,3200) N,WRBF      !GET KHZ LINE FROM FILE
3200  FORMAT(Q,150A1)
      READ  (1,3100)  WDAT(1)
C
      IP = 1
      IP1 = 1
C
3300  DECODE (7,700,WRBF(IP1)) CFRB(IP)  !DECODE KHZ INTO CFR BUFFER
      IP1 = IP1 + 6
      IF (WRBF(IP1) .EQ. ' ') GO TO 3400 !SKIP IF AT END
      IP1 = IP1 + 1
      IP = IP + 1
      GO TO 3300
C
3400  IP1 = 1
C
3500  WRITE (5,2100) 27,12        !ERASE GRAPH SCREEN
C
3600  IPASS = 0
C
      CALL DPIOP(NTYPE)           !SET UP GRAPH
      CALL TCPPLT(1,450,300)       !PUT DATE ON GRAPH
      WRITE  (5,3650)  31,IDATE
3650  FORMAT(1X,1A1,9A1,$)
      CALL TCPPLT(1,450,280)       !PUT FREQ. ON GRAPH
      WRITE  (5,3660)  31,CFRB(IP1)
3660  FORMAT(1X,1A1,F6.3,' KHZ',$)
      CALL TCPPLT(1,450,260)       !PUT FILE NAME ON GRAPH
      WRITE  (5,200)  31,PFIL
      CALL  TCPPLT(1,450,240)
      WRITE  (5,3670)  31,(PTB(J),J=1,IPTB)
3670  FORMAT(1X,1A1,20A1)
      CALL  TCPPLT(1,450,220)
      WRITE  (5,3670)  31,(RIT(J),J=1,IRIT)
C
3700  READ (1,750,END=3800) WDAT      !READ FILE DATA
      IF (WDAT(1) .EQ. 'E') GO TO 3800
      DECODE  (3,650,WDAT(1))  IDB
      DECODE  (7,700,WDAT(5))  DPAMP
      DECODE  (7,700,WDAT(13))  RNOISE
      DBSPL = FLOAT(IDB)
C
      CALL DPIOPL(1,CFRB(IP1),DBSPL,DPAMP,RNOISE,IPASS)  !PLOT IT
      IPASS = 1
      GO TO 3700
C
3800  WRITE (5,3900) 27,23            !SEND GRAPH TO PRINTER
3900  FORMAT(1X,2A1)
C
```

```
      IP1 = IP1 + 1
      IF (IP1 .LE. IP) GO TO 3500
C
4000  CALL CLOSE (1)
      CALL CLOSE (3)
      CALL CLOSE (4)
C
5100  CALL TEKOUT(24)
C
      RETURN
      END
      SUBROUTINE   DPIOP(NTYPE)
C
C     PLOT AXIS, TICS, LABELS, ETC. FOR I/O DP'S
C
C     ************************************************************
C     SUBR STARTS
C
      ITITLE = 1   !PUT TITLES ON PLOT
      IFRL = 1     !LABEL TIC MARKS
C
      CALL DPPLT1(NTYPE,ITITLE,IFRL)  !SET UP GRAPH
      WRITE (5,200) 27,97             !DOTTED GRAPH LINES
200   FORMAT(1X,2A1,$)
C
      DO 250 I = 1,4                  !GRAPH ST. DEV. LINES
      IBP = 1
      CALL DPPLT2(IBP,IPERR)
250   CONTINUE
C
      WRITE (5,200) 27,96             !RESTORE TO SOLID LINES
      RETURN
      END
      SUBROUTINE   DPIOPL(IPL,CFR,DBSPL,DPAMP,RNOISE,IPASS)
C
      DIMENSION  CFRO(4),DBO(4),DPO(4),RNO(4)
C
      COMMON /COM002/ ILOG,LR,IYA,XLO,YLO,XHI,YHI,AX,XLN,XSCALE,YLN,YSCALE
      COMMON /COM004/ CFRO,DBO,DPO,RNO
C
C
*****************************************************************
*****
C     SUBR. STARTS
C
      IX = 375                !MAX X = 325
      IY = 60                 !Y OFFSET BY 60
C
      IF (IPL) GO TO 400
C
      WRITE (5,200) 31,27,127         !ERASE SEQ. FOR MAC
```

```
200    FORMAT(1X,3A1,$)
C
       CALL TCPPLT(1,IX,IY)        !ERASE PREV. TEXT
       WRITE (5,300) 31,CFRO(1),DBO(1),DPO(1),RNO(1) !REWRITE = ERASE
300    FORMAT (1X,1A1,4(' ',F7.3))
C
       CALL TEKOUT(13)
C
       CALL TCPPLT(1,IX,IY)
       WRITE (5,300) 31,CFR,DBSPL,DPAMP,RNOISE
C
400    IBP = 1
       IF (IPASS) IBP = 2
       IF (IPASS) CALL PLTLIN(1,1,IX,IY,1,DBO(1),DPO(1))
       CALL PLTLIN(1,1,IX,IY,IBP,DBSPL,DPAMP)
       CALL PLTCRS(IX,IY,2)
       IF (IPASS) CALL PLTLIN(1,1,IX,IY,1,DBO(1),RNO(1))
       CALL PLTLIN(1,1,IX,IY,IBP,DBSPL,RNOISE)
C
       CFRO(1) = CFR               !UPDATE AS PREV. INFO
       DBO(1) = DBSPL
       DPO(1) = DPAMP
       RNO(1) = RNOISE
C
       RETURN
       END
       SUBROUTINE DPNERR(ISW,IERR,DPKHZ,DPAMP,RNOISE)
C
       BYTE MMKCMD(19)  !"Move marker" command to the analyzer.
       BYTE MKRVAL(54)  !Marker values, as read from the analyzer.
C                       !to confirm there was no error in conversion.
C
C
*******************************************************************
***
C      SUBR. STARTS
C
C ISW = 0 Set the marker to DPkhz and read its amplitude OR
C ISW = 1 Set the marker to DPkhz+50hz to get noise floor amplitude
C
       IERR = 0
       DPT = DPKHZ * 1000.0
       IF (ISW) DPT = DPT+ 50.0
       ENCODE (18, 100, MMKCMD) DPT
100    FORMAT ('MMKP ', F9.3, ' HZ;')
C
105    J = IBUP (0, 16, MMKCMD, 18)
C
C      Read the amplitude.
C
       J = IBUP (0, 16, 'RDMK;', 5)       !Request the marker values.
```

```
      J = IBUP (1, 16, MKRVAL, 54)      !Read the marker values.
C
110   J = IBUP (6, 16)                 !Poll the analyzer.
      IF (J .AND. 32) GO TO 200
      IF (J .AND. 17) GO TO 111
      GO TO 110
C
111   DECODE (16, 115, MKRVAL(22),ERR=300) DPT
115   FORMAT (E16.3)
      GO TO 500
C
200   J = IBUP (0, 16, 'ERR?;', 5)
      GO TO 105
C
C We have detected that invalid data has been received from the analyzer.
C
300   IERR = 1
C
      WRITE  (5,410)  24,(MKRVAL(J),J=22,37),DPT,7,7
410   FORMAT (/1X,1A1,'ERROR ',16A1,'  ',F9.2,2A1)
      RETURN
C
500   IF (DPT .LT. -99.999 .OR. DPT .GT. 999.999) IERR = 1
C
      IF  (IERR)  WRITE  (5,510)  24,(MKRVAL(J),J=22,37),7,7
510   FORMAT(1X,1A1,'MARKER ERROR, VALUE = ',16A1,2A1)
C
      IF (.NOT. (ISW)) DPAMP = DPT
      IF (ISW) RNOISE = DPT
C
      RETURN
      END
      SUBROUTINE   DPPLT1(NTYPE,ITITLE,IFRL)
C
      BYTE XSTR(23),YSTR(20)
C
      COMMON /COM002/ ILOG,LR,IYA,XLO,YLO,XHI,YHI,AX,XLN,XSCALE,YLN,YSCALE
      COMMON /COM005/ XINC,XLBINC,YINC,YLBINC
C
      DATA  YSTR  /'  ','D','P','  ','A','M','P','L','I','T','U','D','E',
     +          ' ','d','B','  ','S','P','L'/
C
C     ******************************************************************
C     SUBR. STARTS
C
C     PLOT X/Y AXIS
C
      CALL PLAXIS              !GO PLOT X/Y AXIS
C
      IF (.NOT. (ILOG)) GO TO 50
      CALL LBLXLG(IFRL)
```

```
      GO TO 500
C
50    X = XLO              !START WITH 1ST X...
      Y = YLO              !...AND Y
      X1 = XLO             !SAVE 1ST TIC LOCATION
C
C     PLOT X TICS, LABELS
C
100   CALL PLTLIN(1,1,IX,IY,1,X,Y)           !INIT PLOT CURSOR
      IYM = IY - 5                   !EXTEND Y FOR TIC
      IX1 = INT(X * 10.0)
      IX2 = INT(X1 * 10.0)
      IF (IX1 .EQ. IX2) IYM = IYM - 5  !EXTEND TIC FOR LABEL
      CALL TCPPLT(2,IX,IYM)                  !PLOT LINE
      IF (IX1 .NE. IX2) GO TO 450    !SKIP IF NO LABEL
      IF (IFRL .EQ. 0) GO TO 400  !SKIP IF NO LABEL
      IYM = IYM - 10                  !ELSE, CURSOR DOWN...
      IXM = IX - 10                   !...AND LEFT
      CALL TCPPLT(1,IXM,IYM)                 !POSITION CURSOR
      IX3 = MOD(IX1,10)
      IF (.NOT. (IX3)) WRITE (5,200) 31,INT(X)
      IF (IX3) WRITE (5,210) 31,X
200   FORMAT(1X,1A1,I3)
210   FORMAT(1X,1A1,F3.1)
C
400   X1 = X1 + XLBINC                  !BUMP TIC INCRE.
C
450   X = X + XINC                    !BUMP X INCRE.
      IF (X .LE. XHI) GO TO 100          !LOOP 'TIL END
C
C     X TITLE
C
500   CALL TCPPLT(1,100,8)
C
      IF (.NOT. (ITITLE)) GO TO 520
      IF (NTYPE .EQ. 0) CALL INSERT ('PRIMARY LEVELS (dB SPL)',XSTR,1,23)
      IF (NTYPE .EQ. 1) CALL INSERT ('      FREQ. (KHZ)      ',XSTR,1,23)
      IF (NTYPE .EQ. 2) CALL INSERT ('      F2/F1 RATIO      ',XSTR,1,23)
C
      WRITE (5,510) 31,XSTR        !WRITE TITLE
510   FORMAT(1X,1A1,23A1)
C
C     PLOT Y TICS, LABELS
C
520   X = XLO          !SAME COMMENTS AS ABOVE (EXCEPT FOR LOG)
      Y = YLO
      Y1 = YLO
C
550   CALL PLTLIN(1,1,IX,IY,1,X,Y)
      IXM = IX - 5
      IF (Y .EQ. Y1) IXM = IXM - 5
```

```
      CALL TCPPLT(2,IXM,IY)
      IF (Y .NE. Y1) GO TO 700
      IXM = IXM - 25
      IYM = IY - 5
      CALL TCPPLT(1,IXM,IYM)
      WRITE (5,600) 31,INT(Y)
600   FORMAT(1X,1A1,I3)
      Y1 = Y1 + YLBINC
C
700   Y = Y + YINC
      IF (Y .LE. YHI) GO TO 550
C
      IF (.NOT. (ITITLE)) RETURN
      IY = 300
C
      DO 800 I = 1,20         !PRINT CHARACTERS VERTICALLY
      CALL TCPPLT(1,8,IY)       !TOP OF THE TITLE
      WRITE (5,750) 31,YSTR(I)
750   FORMAT(1X,1A1,1A1)
      IY = IY - 10
800   CONTINUE
C
      RETURN
      END
      SUBROUTINE   DPPLT2(IBP,IPERR)
C
C     *************************************************************
C     SUBR. STARTS
C
      IPERR = 0
C
100   READ (4,200,ERR=100,END=300) X,Y  !READ ST.DEV DATA
200   FORMAT(2F9.3)
C
      IF (X .EQ. 0.0 .AND. Y .EQ. 0.0) GO TO 100
C
      IF (X .EQ. 999.0) RETURN          !END OF DATA TEST
      CALL PLTLIN(1,1,IX,IY,IBP,X,Y)       !PLOT THE DATA
      IBP = 2                          !DON'T INIT PLOT ANYMORE
      GO TO 100                         !LOOP FOR MORE DATA
C
300   IPERR = 1
      RETURN
      END
      SUBROUTINE   DPPPRM(NTYPE,CRIT,NBRAVG,SPAN,STP,IGP,ICOR)
C
      BYTE SP
      BYTE CORFIL(11),GRFILE(11),XFRFIL(16),RTYPE,NFR,PRSW,GRD,SJT,AFT
C
      COMMON /COM001/ CORFIL,GRFILE,XFRFIL,RTYPE,NFR,PRSW,GRD,SJT,AFT
C
```

```
C
*****************************************************************
*
C     SUBR. STARTS
C
      SP = ' '
      CALL SCFUNC(1,N,N)       !CLEAR SCREEN
      CALL SCFUNC(3,2,1)       !POSN. CURSOR LINE 2, COL 1
      WRITE (5,20)
20    FORMAT(1X,'DEFAULT SETTINGS - AT THE "ENTER OPTION" PROMPT:'/1X,
   + 'SELECT A LETTER IN THE OPTION COLUMN TO CHANGE A DEFAULT SETTING.'/)
C
      WRITE (5,100) NBRAVG,SPAN,PRSW,CORFIL,GRFILE,NFR,CRIT,GRD,STP,
   + SJT,AFT,RTYPE
100   FORMAT(1X,
   + 'OPTION  SETTING   FUNCTION'/1X,
        +      '------      ---------          ---------------------------------'/1X,
   + ' A  ',I6,'      NUMBER OF SIGNAL ANALYZER AVERAGES'/1X,
   + ' F  ',F7.3,' kHz  FREQUENCY SPAN OF ANALYZER WINDOW'/1X,
   + ' P       ',1A1,'       ECHO SCREEN TO PRINTER'/1X,
   + ' D  ',11A1,'  DPE AMPLITUDE CORRECTION FILE'/1X,
   + ' G  ',11A1,'  GRAPH PARAMETER AND AV. +- STDEV FILE'/1X,
   + ' N       ',1A1,'       USE NOISE FLOOR REJECTION SUBROUTINE'/1X,
   + ' C  ',F7.3,'      NOISE FLOOR REJECTION CRITERION'/1X,
   + ' M       ',1A1,'       DUMP GRAPHICS AT END OF RUN'/1X,
   + ' S  ',F7.3,'      DP AMP/NF DIFFERENCE STOP POINT'/1X,
   + ' B       ',1A1,'       SUBJECT TYPE'/1X,
   + ' T       ',1A1,'       AUTO TRANSFER TO MACINTOSH'/1X,
   + ' R       ',1A1,'       RUN TYPE'//1X,
   + ' X              EXIT MENU, CONTINUE WITH RUN'//$1X,
   + 'ENTER OPTION: ')
C
120   CALL SCFUNC(3,22,15)
C
      WRITE (5,130) 27         !WAS SPACE @ 350
130   FORMAT(1X,1A1,'[J',$)
C     CALL SCFUNC(3,22,15)
      CALL IPOKE("44, IPEEK("44) .OR. "050100)
C
150   KEY = ITTINR()           !FLUSH ANY PREV. KEYS
      IF (KEY .GE. 0) GO TO 150
C
200   KEY = ITTINR()           !READ KEYBOARD
      IF (KEY .LT. 0) GO TO 200     !LOOP IF NO INPUT
C
      KEY = KEY .AND. "177
      IF (KEY .GT. 90) KEY = KEY - 32
      CALL IPOKE("44,IPEEK("44) .AND. (.NOT. "050100))
C
      IF (KEY .EQ. 88) GO TO 9000
      IF (KEY .LT. 65 .OR. KEY .GT. 84) GO TO 8000
```

```
C
300   CALL SCFUNC(3,22,15)
C
      WRITE (5,350) KEY
350   FORMAT(1X,1A1,$)
C
      CALL SCFUNC(3,23,1)
      WRITE (5,400) 27
400   FORMAT(1X,1A1,'[0J',$)
      CALL SCFUNC(3,23,1)
C
      KEY = KEY - 64
      CALL SCFUNC(3,22,21)
C
C            A   B   C   D   E   F   G   H   I   J   K
      GO  TO  (1000,1100,1200,1520,8000,1500,1600,8000,8000,8000,8000,
     +         8000,1900,2000,8000,2100,8000,2400,1280,2300) KEY
C            L   M   N   O   P   Q   R   S   T
C
1000  WRITE (5,1010)
1010  FORMAT(1X,'ENTER VALUE : '$)
C
      READ (5,1050) NBRAVG
1050  FORMAT(I6)
C
      CALL SCFUNC(3,7,7)
      WRITE (5,1060) NBRAVG
1060  FORMAT(1X,I6,$)
      GO TO 120
C
1100  WRITE (5,1110)
1110  FORMAT(1X,'ENTER SUBJECT TYPE: '$)
C
      READ (5,1120) SJT
1120  FORMAT(1A1)
C
      CALL SCFUNC(3,16,12)
      WRITE (5,1150) SJT
1150  FORMAT(1X,1A1,$)
      GO TO 120
C
1200  WRITE (5,1010)
C
      READ (5,1250) CRIT
1250  FORMAT(F10.0)
C
      CALL SCFUNC(3,13,7)
      WRITE (5,1260) CRIT
1260  FORMAT(1X,F7.3,$)
      GO TO 120
C
```

```
1280 WRITE  (5,1010)
C
     READ (5,1250) STP
C
     CALL SCFUNC(3,15,7)
     WRITE (5,1260) STP
     GO TO 120
C
1500 WRITE  (5,1010)
C
     READ (5,1250) SPAN
C
     CALL SCFUNC(3,8,7)
     WRITE (5,1260) SPAN
     GO TO 120
C
1520 WRITE  (5,1610)
C
     READ (5,1620) CORFIL
C
     ICOR = 1
     CALL FILXST(IX,CORFIL)
     IF (IX .GT. 0) GO TO 1540
     ICOR = 0
     CALL TEKOUT(7)
     CALL INSERT ('NO FILE    ',CORFIL,1,11)
C
1540 CALL SCFUNC(3,10,7)
     WRITE (5,1660) CORFIL
     GO TO 120
C
1600 WRITE  (5,1610)
1610 FORMAT(1X,'ENTER FILE: ',$)
C
     READ (5,1620) GRFILE
1620 FORMAT(11A1)
C
     IGP = 1
     CALL FILXST(IX,GRFILE)
     IF (IX .GT. 0) GO TO 1640
     IGP = 0
     CALL TEKOUT(7)
     CALL INSERT ('NO FILE    ',GRFILE,1,11)
C
1640 CALL SCFUNC(3,11,7)
     WRITE (5,1660) GRFILE
1660 FORMAT(1X,11A1,$)
     GO TO 120
C
1900 IF (GRD .EQ. 'Y') GO TO 1910
     GRD = 'Y'
```

```
      GO TO 1920
C
1910  GRD = 'N'
C
1920  CALL SCFUNC(3,14,12)
      WRITE (5,1150) GRD
      GO TO 120
C
2000  IF (NFR .EQ. 'Y') GO TO 2010
      NFR = 'Y'
      GO TO 2020
C
2010  NFR = 'N'
C
2020  CALL SCFUNC(3,12,12)
      WRITE (5,1150) NFR
      GO TO 120
C
2100  IF (PRSW .EQ. 'Y') GO TO 2110
      PRSW = 'Y'
      GO TO 2120
C
2110  PRSW = 'N'
C
2120  CALL SCFUNC(3,9,12)
      WRITE (5,1150) PRSW
      GO TO 120
C
2300  IF (AFT .EQ. 'Y') GO TO 2310
      AFT = 'Y'
      GO TO 2320
C
2310  AFT = 'N'
C
2320  CALL SCFUNC(3,17,12)
      WRITE (5,1150) AFT
      GO TO 120
C
2400  WRITE (5,2410)
2410  FORMAT(1X,'ENTER RUN TYPE: '$)
C
      READ (5,1120) RTYPE
C
      CALL SCFUNC(3,18,12)
      WRITE (5,1150) RTYPE
      GO TO 120
C
8000  CALL TEKOUT(7)
      CALL SCFUNC(3,22,15)
      WRITE (5,350) SP
      GO TO 120
```

```
C
9000 RETURN
     END
     SUBROUTINE  DPPRNT(IPF,NTYPE,CFR,DBSPL,DPAMP,RNOISE,PFIL)
C
     BYTE  PTB(20),RIT(20)
     BYTE  IDATE(9),PFIL(10)
C
     COMMON /COM009/ IPTB,IRIT,PTB,RIT
C
C    ***************************************************************
C    SUBR. STARTS
C
     OPEN (UNIT=6, NAME='LP:', CARRIAGECONTROL='FORTRAN')
C
     GO  TO  (100,200,300,400,500)  IPF
C
C    IPF = 1...FORM FEED AND DATE
C
100  CALL DATE(IDATE)           !GET THE DATE
C
     WRITE  (6,105)  12,IDATE
     WRITE  (6,110)  PFIL
105  FORMAT(1X,1A1,'DATE  : '9A1)
110  FORMAT(1X,'FILE  : '10A1)
C
     WRITE  (6,120)  (PTB(J),J=1,IPTB)
     WRITE  (6,130)  (RIT(J),J=1,IRIT)
120  FORMAT(1X,'TITLE : ',20A1)
130  FORMAT(1X,'RUN ID: ',20A1/)
C
     GO TO 1000
C
C    IPF = 2...HEADER FOR A OR R TYPES
C
200  IF (NTYPE .EQ. 1) WRITE (6,210)
     IF (NTYPE .EQ. 2) WRITE (6,220)
210  FORMAT(/1X,'  FREQ.    dBSPL    DP AMP.    NS. AMP.')
220  FORMAT(/1X,'  RATIO    dBSPL    DP AMP.    NS. AMP.')
     GO TO 1000
C
C    IPF = 3...HEADER FOR I/O TYPE
C
300  WRITE  (6,310)  CFR
310  FORMAT(/1X,F9.3,' KHZ      DP AMP        NS AMP')
     GO TO 1000
C
C    IPF = 4...DATA FOR I/O TYPE
C
400  WRITE (6,410) DBSPL,DPAMP,RNOISE
410  FORMAT('+',T5,F6.2,T22,F6.2,T37,F6.2)
```

```
      GO TO 1000
C
C     IPF = 5...DATA FOR A OR R TYPE
C
500   WRITE (6,510) CFR,DBSPL,DPAMP,RNOISE
510   FORMAT('+',F9.3,T16,F6.2,T28,F6.2,T41,F6.2)
C
1000  CLOSE (UNIT=6)
C
      RETURN
      END
      SUBROUTINE DPSYN
C
      COMMON /COM003/ DPKHZ,FAKHZ,FAATTN,FBKHZ,FBATTN
      COMMON /COM006/ RNOISE,DPAMP
C
C
****************************************************************
*******
C     SUBR. STARTS
C
C     Set synthesizer frequency, attenuation
C
400   CALL HPCHAN ('A')
      CALL HPATTN (FAATTN)          !for channel A;
      CALL HPCHAN ('B')
      CALL HPATTN (FBATTN)          !for channel B.
C
C Initiate an averaged measurement of the signal at the analyzer
C and wait for average to be complete.
C
      J = IBUP (0, 16, 'RSRQ; STRT; ERR?;', 17)
C
450   J = IBUP (6, 16)              !Poll the analyzer.
      IF ((J.AND.001).EQ..FALSE.) GO TO 450     !LOOP 'TILL FINISHED
C
C Get the marker values for both DPAMP and the NOISE floor.
C
      CALL DPNERR(0,IERR,DPKHZ,DPAMP,RNOISE)
      IF (IERR) GO TO 400
      CALL DPNERR(1,IERR,DPKHZ,DPAMP,RNOISE)
      IF (IERR) GO TO 400
C
      RETURN
      END
      SUBROUTINE   DPVERF(IFN,FIL)
C
C     SEARCHES BY 10'S, THEN BY 1'S (VIA FILE EXTENSION NUMBER),
C     FOR THE NEXT AVAILABLE FILE EXTENSION NUMBER.
C
      BYTE  FIL(16)
```

```
C
C
***************************************************************
**
C
      IFN = 11               !START AT FILE EXTENSION 11
      INC = 10                !SEARCH BY 10'S
      IRET = 1                !RETURN TO 50
      GO TO 100
C
50    INC = 1               !NOW, SEARCH BY 1'S
      IFN = IFN - 10            !ADJUST FILE NUMBER
      IRET = 0              !RETURN TO CALLER
C
100   CALL DPCDFX(IFN,FIL)       !ENCODE EXTEN. TO NAME
C
      CALL FILXST(IX,FIL)
      IF (IX .LE. 0) GO TO 200
      IFN = IFN + INC                   !YES, KEEP SEARCHING
      GO TO 100
C
200   IF (IRET) GO TO 50
C
      CALL CLOSE (4)
      RETURN
      END
      SUBROUTINE   FILXST(IX,FILE)
C
C
***************************************************************
*
C     PURPOSE:  VERIFIES THE EXISTENCE OF A FILE SPECIFIED BY
C            THE CALLER.
C
C      INPUTS:  FILE   UP TO 15 BYTES OF A FILE NAME
C     OUTPUTS:  IX     NEGATIVE = FILE DOESN'T EXIST
C                   POSITIVE = FILE'S LENGTH IN BLOCKS
C
C
***************************************************************
*
C
      BYTE  FILE(16),TMPBUF(13)
      DIMENSION  IAB(6)
C
C
***************************************************************
*
C     BEGIN
C
C     PREPARE TMPBUF FOR LOOKUP BUFFER.  SY IS DEVICE DEFAULT
```

```
C
      CALL INSERT ('SY          ',TMPBUF,1,12) !SET TEMP. BUFFER
      TMPBUF(13) = 0
C
      ICLN = INDEX(FILE,':')    !FIND COLON, IF DEVICE SPECIFIED
      IF (ICLN .GT. 4) ICLN = 0
      IPER = INDEX(FILE,'.')    !FIND EXTENSION PERIOD
C
C     ***********************************************
C     XFER DEVICE FROM PARAMETER FILE TO TMPBUF
C
      IF (ICLN .EQ. 0) GO TO 10    !SKIP IF NO DEVICE SPECIFIED
      I = ICLN - 1              !DEVICE BYTE LENGTH
      CALL INSERT (FILE,TMPBUF,1,I) !BUFFER XFER
      CALL IRAD50 (3,TMPBUF,IDEV)
      IFF = IFETCH(IDEV)
      IF (IFF) PAUSE 'DEVICE ERROR'
C
C     ********************************************
C     XFER NAME FROM PARAMETER FILE TO TMPBUF
C
10    I = ICLN + 1              !1ST BYTE AFTER DEVICE
      IBOD = IPER - I           !FILE BODY NAME LENGTH
      CALL INSERT (FILE(I),TMPBUF,4,IBOD)
C
C     **************************************************
C     XFER EXTENSION FROM PARAMETER FILE TO TMPBUF
C
      I = IPER + 1
      CALL INSERT (FILE(I),TMPBUF,10,3)  !FILE EXTENSION
C
C     RADIX TMPBUF, LOOKUP FILE
C
      CALL IRAD50 (12,TMPBUF,IAB)
      ICH = IGETC()             !GET A CHANNEL
      IX = LOOKUP(ICH,IAB)      !LOOK UP FILE
      CALL ICLOSE (ICH,I)
      CALL IFREEC(ICH)          !FREE THE CHANNEL
C
      RETURN
      END
      SUBROUTINE GPFPRM(NTYPE,GPFFIL)
C
      BYTE BLOG,CLRG(2),CLRS(4),GPFFIL(11)
C
      COMMON /COM002/ ILOG,LR,IYA,XLO,YLO,XHI,YHI,AX,XLN,XSCALE,YLN,YSCALE
      COMMON /COM005/ XINC,XLBINC,YINC,YLBINC
C
      DATA CLRG /27,12/                     !CLEAR GRAPH
      DATA CLRS  /27,'[','2','J'/
C
```

```
C
***********************************************************************
********
C       SUBR.STARTS
C
        WRITE (5,5) CLRS,CLRG   !CLEAR SCREEN, GRAPH
5       FORMAT(1X,4A1,2A1)
C
C       NTYPE = 0 FOR "I" TYPE GPF FILES.
C
        XLN = 300.0             !X LENGTH IN PIXELS
        YLN = 300.0             !Y LENGTH
        IF (.NOT. (NTYPE)) GO TO 10
        XLN = 300.0             !"A" OR "R" TYPE FILES
        YLN = 135.0
C
10      CALL ASSIGN(4,GPFFIL)
        READ (4,20) BLOG        !LOG. FLAG
20      FORMAT(1A1)
C
        ILOG = 0
        IF (BLOG .EQ. 'Y') ILOG = 1
C
        READ(4,50)XLO           !LEAST X
        READ(4,50)XHI           !MOST X
        READ(4,50)YLO           !SAME FOR Y'S
        READ(4,50)YHI
        YSCALE = YHI - YLO      !Y PLOT SCALE
        IF(ILOG) GO TO 30       !SKIP XTICS & LABELS IF IN LOG SCALE
        AX = XLO                !ELSE, XLO NOT LOG
        XSCALE = XHI - AX       !NEITHER IS XSCALE
        READ(4,50)XINC          !TIC INCREMENT
        READ(4,50)XLBINC        !LABEL INCREMENT
        XST = XSCALE / XLBINC   !HOW MANY TICS
        GO TO 40
C
30      IF (.NOT. (NTYPE)) GO TO 35
        XLO = XLO / 1000.0
        XHI = XHI / 1000.0
C
35      AX = ALOG10(XLO)        !LOG X'S
        XSCALE = ALOG10(XHI) - AX
        XST = 1                 !LOW TICK COUNT
C
40      READ(4,50)YINC          !Y TIC INC.
        READ(4,50)YLBINC        !Y LABEL INC.
50      FORMAT(F7.0)
C
        RETURN
        END
        SUBROUTINE  LBLXLG(IFRL)
```

```
C
        COMMON /COM002/ ILOG,LR,IYA,XLO,YLO,XHI,YHI,AX,XLN,XSCALE,YLN,YSCALE
C
C       ******************************************************************
C       SUBR. STARTS
C
        Y = YLO                   !Y LOW
        XINC = 0.1                 !X TIC INCREMENT
        XTIC = 0.1                !START XTIC
        XTGT = 1.0                 !X TARGET
        XLBL = XLO                  !1ST X LABEL = X LOW
        IXT  = INT(XTIC * 10.0)
        IXL  = INT(XLBL * 10.0)
        IXTG = INT(XTGT * 10.0)
C
100     IF (IXT .EQ. IXL) GO TO 200     !CLIMBING UP TO X LOW
        XTIC = XTIC + XINC            !NOT YET, INCREMENT X TIC
        IXT  = INT(XTIC * 10.0)
        IF (IXT .LT. IXTG) GO TO 100   !REPEAT IF NOT AT X TARGET
        XINC = XINC * 10.0            !ELSE, MAKE NEXT MULT. OF 10
        XTGT = XTGT * 10.0
        IXTG = INT(XTGT * 10.0)
        GO TO 100                  !RETRY
C
200     CALL PLTLIN(1,1,IX,IY,1,XTIC,Y)          !TIC LOCATION
        IYM = IY - 5                   !Y TARGET FOR TIC
        CALL TCPPLT(2,IX,IYM)                !PLOT TIC
        IF (IXT .NE. IXL) GO TO 600         !SKIP IF NO EXTEND TIC
        IYM = IYM - 5                  !EXTEND TIC FOR LABEL
        CALL TCPPLT(2,IX,IYM)                !PLOT IT
        IF (.NOT. (IFRL)) GO TO 600          !SKIP IF NO LABEL
        IYM = IYM - 10                 !MOVE CURSOR DOWN...
        IXM = IX - 10                  !...AND LEFT
        CALL TCPPLT(1,IXM,IYM)              !POSITION CURSOR
        IF (XTIC .LT. 1.0) WRITE (5,400) 31,XTIC       !DISPLAY X (.N)
        IF (XTIC .GT. 99.0) WRITE (5,500) 31,INT(XTIC) !         (NN)
        IF (XTIC .GE. 1.0 .AND. XTIC .LT. 100.0) WRITE (5,300) 31,INT(XTIC)
300     FORMAT(1X,1A1,I2,$)
400     FORMAT(1X,1A1,F3.1,$)
500     FORMAT(1X,1A1,I3,$)
C
600     XTIC = XTIC + XINC            !BUMP FOR NEXT TIC
        IXT  = INT(XTIC * 10.0)
        IF (XTIC .GT. XHI) RETURN        !END IF PAST X HIGH
        IF (IXT .LT. IXTG) GO TO 700     !SKIP IF NOT AT X TARGET
        XINC = XINC * 10.0            !ELSE, NEXT MULTIPLE OF 10
        XTGT = XTGT * 10.0
        IXTG = INT(XTGT * 10.0)
C
700     IXTST = INT(XINC * 10.0)
        IF (IXT .EQ. IXTST) XLBL = XTIC
```

```
      IF (IXT .EQ. (2 * IXTST)) XLBL = XTIC
      IF (IXT .EQ. (5 * IXTST)) XLBL = XTIC
      IXL = INT(XLBL * 10.0)
      GO TO 200
C
      END
      SUBROUTINE  MACTIT(XFRFIL,DSPF,RTYPE,SJT)
C
      BYTE  PTB(20),RIT(20),XFRFIL(16),DSPF(10),FNAM(4),EAR,RTYPE,SJT
C
      COMMON /COM009/ IPTB,IRIT,PTB,RIT
C
C
****************************************************************
C     SUBR STARTS
C
      EAR = ' '
      DO 20 I = 1,20
      PTB(I) = ' '
      RIT(I) = ' '
      IF (I .LT. 5) FNAM(I) = ' '
      IF (I .LT. 11) DSPF(I) = ' '
20    CONTINUE
C
      CALL SCFUNC(1,N,N)
C
50    CALL SCFUNC(3,3,0)
      WRITE  (5,100)
100   FORMAT(1X,
   + '1. ENTER PROJECT TITLE (AS IN MAC FOLDER NAME, 20 CHARS MAX):')
C
150   CALL SCFUNC(3,6,0)
      WRITE  (5,200)
200   FORMAT(1X,'2. ENTER RUN IDENTIFICATION TITLE (20 CHARS MAX):')
C
250   CALL   SCFUNC(3,9,0)
      WRITE  (5,300)
300   FORMAT(1X,'3. ENTER BASE FILE NAME (4 CHARS. MAX.): ')
C
350   CALL SCFUNC(3,11,0)
      WRITE  (5,400)
400   FORMAT(1X,'4. ENTER EAR (R OR L): ')
C
      IP = 0
      GO TO 1000
C
600   GO  TO  (1000,1100,1200,1300)  LP
C
1000  CALL SCFUNC(3,4,4)
      WRITE  (5,1010)
1010  FORMAT(1X,'____________________',$)
```

```
      CALL SCFUNC(3,4,4)
      READ (5,1020) IPTB,PTB
1020  FORMAT(Q,20A1)
C
      IF (IPTB .LT. 21) GO TO 1090
      IPTB = 20
      CALL SCFUNC(3,4,24)
      WRITE (5,1030) 27
1030  FORMAT(1X,1A1,'[K')
C
1090  IF (IP) GO TO 2000
C
1100  CALL SCFUNC(3,7,4)
      WRITE (5,1010)
      CALL SCFUNC(3,7,4)
      READ (5,1020) IRIT,RIT
      IF (IRIT .LT. 21) GO TO 1190
      IRIT = 20
      CALL SCFUNC(3,7,24)
      WRITE (5,1030) 27
C
1190  IF (IP) GO TO 2000
C
1200  CALL SCFUNC(3,9,42)
      WRITE (5,1210)
1210  FORMAT(1X,'____',$)
      CALL SCFUNC(3,9,42)
      READ (5,1220) IFL,FNAM
1220  FORMAT(Q,4A1)
      IF (.NOT. (IFL)) CALL TEKOUT(7)
      IF (.NOT. (IFL)) GO TO 1200
      IF (IP) GO TO 2000
C
1300  CALL SCFUNC(3,11,24)
      WRITE (5,1310)
1310  FORMAT(1X,'_',$)
      CALL SCFUNC(3,11,24)
      READ (5,1320) EAR
1320  FORMAT(1A1)
C
2000  IP = 1
      CALL SCFUNC(3,15,0)
      WRITE (5,2100) 27
2100  FORMAT(1X,1A1,'[J')
C
      CALL SCFUNC(3,15,0)
      WRITE (5,2200)
2200  FORMAT($1X,'CONTINUE? [Y/N]: ')
C
      READ (5,1320) YN
      IF (YN .EQ. 'Y') GO TO 3000
```

```
C
      WRITE  (5,2300)
2300  FORMAT(/$1X,'SELECT ENTRY TO CHANGE [1/2/3/4]: ')
C
      READ  (5,2400)  LP
2400  FORMAT(I1)
C
      GO TO 600
C
3000  CALL INSERT(FNAM,XFRFIL,5,IFL)
      IP = IFL + 5
      XFRFIL(IP) = EAR
      XFRFIL(IP+1) = RTYPE
      XFRFIL(IP+2) = '.'
      CALL DPVERF(I,XFRFIL)
      IP = IFL + 6
      CALL INSERT(XFRFIL(5),DSPF,1,IP)
C
      CALL ASSIGN(1,XFRFIL)
C
      WRITE  (1,4000)  RTYPE
4000  FORMAT(1A1)
C
      WRITE  (1,4000)  SJT
C
      WRITE  (1,4100)  (DSPF(J),J=1,IP)
4100  FORMAT(10A1)
C
      WRITE  (1,4200)  (PTB(J),J=1,IPTB)
4200  FORMAT(20A1)
C
      WRITE  (1,4200)  (RIT(J),J=1,IRIT)
C
      RETURN
      END
      SUBROUTINE  NSFLRJ(TN,CRIT,CORR,IPASS,NFR)
C
      BYTE NFR
C
      DIMENSION  TDPAMP(4),TNFAMP(4)
C
      COMMON /COM006/ RNOISE,DPAMP
C
C
*****************************************************************
C     SUBR. STARTS
C
      IF (NFR .EQ. 'Y') GO TO 50
      CALL DPSYN
      DPAMP = DPAMP + CORR
      RNOISE = RNOISE + CORR
```

```
      RETURN
C
50    IF (IPASS) GO TO 200  !SKIP IF NOT INITIAL PASS
C
C     ****************************************
C     INITIAL PASS NOISE FLOOR REJECTION
C
      DO 100 I = 1,4       !GET 4 VALUES OF DPAMP & RNOISE
      CALL DPSYN           !GET AMPLITUDES
      TDPAMP(I) = DPAMP    !SAVE DP
      TNFAMP(I) = RNOISE   !SAVE NOISE
100   CONTINUE
C
      GO TO 500            !GO GET SMALLEST NOISE VALUE
C
C     ****************************************
C
C     SUBSEQUENT NOISE FLOOR REJECTIONS
C
200   ISV = 1
C
300   CALL DPSYN
      TDPAMP(ISV) = DPAMP    !SAVE DP
      TNFAMP(ISV) = RNOISE   !SAVE NOISE
C
      IF (TNFAMP(ISV) .LT. (TN + CRIT)) GO TO 400 !NOISE VS CRIT TEST
C
C     NOISE TEST FAILURE - RETRY UP TO 4 TIMES FOR A LESSER
C     NOISE VALUE.
C
      IF (ISV .EQ. 4) GO TO 500    !SKIP IF END OF BUFFERS
      ISV = ISV + 1                !ELSE, BUMP POINTER
      GO TO 300                    !RETRY
C
C     LESS THAN 4 RETRY FAILURES - GET LEAST NOISE VALUE WITH
C     CORRESPONDING DPAMP.
C
400   IF (TNFAMP(ISV) .LT. TN) TN = TNFAMP(ISV)
      GO TO 700
C
C     GET LEAST NOISE VALUE WITH CORRESPONDING DPAMP
C
500   ISV = 1
      TN = TNFAMP(1)        !INIT. VALUE WITH 1ST OF 4
C
      DO 600 I = 2,4                !LOOP THRU REST
      IF (TNFAMP(I) .LT. TN) ISV = I    !COMPARE FOR LOWEST
600   CONTINUE
C
      TN = TNFAMP(ISV)              !TNFAMP(ISV) WAS LOWEST
C
```

```
700     DPAMP = TDPAMP(ISV) + CORR
        RNOISE = TNFAMP(ISV) + CORR
C
        RETURN
        END
        SUBROUTINE  PLAXIS
C
        COMMON /COM002/ ILOG,LR,IYA,XLO,YLO,XHI,YHI,AX,XLN,XSCALE,YLN,YSCALE
C
C
*****************************************************************
*****
C       SUBR. STARTS
C
        X = XLO                        !CURSOR TO XLO,YLO
        Y = YLO
        CALL  PLTLIN(1,1,IX,IY,1,X,Y)
C
        IXS = IX
        IYS = IY
        X = XHI                        !LINE TO XHI
        CALL  PLTLIN(1,0,IX,IY,2,X,Y)
C
        CALL TCPPLT(1,IXS,IYS)         !CURSOR TO XLO,YLO
        IX = IXS
C
        Y = YHI                        !LINE TO YHI
        CALL  PLTLIN(0,1,IX,IY,2,X,Y)
C
        RETURN
        END
        SUBROUTINE   PLTCRS(IX,IY,ISIZ)
C
C        **************************************************************
C       SUBR. STARTS
C
C       PLOT A CROSS, +/- 10 OR 3 ON X AND Y
C
        IYP = IY + ISIZ
        IYM = IY - ISIZ
        IXP = IX + ISIZ
        IXM = IX - ISIZ
C
        IF (IXM .LT. 0) IXM = 0
        IF (IXP .LT. 0) IXP = 0
        IF (IYM .LT. 0) IYM = 0
        IF (IYP .LT. 0) IYP = 0
        IF (IYM .GT. 479) IYM = 479
        IF (IYP .GT. 479) IYP = 479
C
C       MAKE A CROSS
```

```
C
      CALL TCPPLT(2,IX,IYM)  !DOWN FROM CENTER
      CALL TCPPLT(2,IX,IYP)  !UP FROM CENTER
      CALL TCPPLT(2,IX,IY)  !TO CENTER
      CALL TCPPLT(2,IXM,IY)  !LEFT FROM CENTER
      CALL TCPPLT(2,IXP,IY)  !RIGHT FROM CENTER
C
C     CONNECT THE ENDS
C
      CALL TCPPLT(2,IX,IYM)
      CALL TCPPLT(2,IXM,IY)
      CALL TCPPLT(2,IX,IYP)
      CALL TCPPLT(2,IXP,IY)
C
      RETURN
      END
      SUBROUTINE   PLTLIN(IXS,IYS,IX,IY,IB1,X,Y)
C
      COMMON /COM002/ ILOG,LR,IYA,XLO,YLO,XHI,YHI,AX,XLN,XSCALE,YLN,YSCALE
C
C
****************************************************************
*****
C     SUBR. STARTS
C
      IF (.NOT. (IXS)) GO TO 100
      XX = X
      IF (ILOG) XX = ALOG10(X)
      IX = INT((XX - AX) * (XLN / XSCALE)) + LR
C
100   IF (.NOT. (IYS)) GO TO 200
      IY = INT((Y - YLO) * (YLN / YSCALE)) + IYA
C
200   IF (IX .LT. 0) IX = 0
      IF (IY .LT. 0) IY = 0
      IF (IY .GT. 479) IY = 479
      CALL TCPPLT(IB1,IX,IY)
C
      RETURN
      END
      SUBROUTINE   RDCNFL(IFUN,IERR,NBRAVG,SPAN,CRIT)
C
      BYTE SETNAM(6)
      BYTE CORFIL(11),GRFILE(11),XFRFIL(16),RTYPE,NFR,PRSW,GRD,SJT,AFT
C
      COMMON /COM001/ CORFIL,GRFILE,XFRFIL,RTYPE,NFR,PRSW,GRD,SJT,AFT
      COMMON /COM003/ DPKHZ,FAKHZ,FAATTN,FBKHZ,FBATTN,DBSPL,STZ,STP,TDB
      COMMON /COM010/ SETNAM
C
```

```
C
*****************************************************************
*
C     SUBR STARTS
C
      IERR = 0
      GO TO (100,200) IFUN
C
C     ******************************************
C     INIT. READ
C
100   READ (2,110) SETNAM
      READ (2,110) SETNAM
110   FORMAT(2X,6A1)
C
      READ (2,120,ERR=130) SETNAM,RATTN,NBRAVG,STP,SPAN,CORFIL,
 +        NFR,CRIT,PRSW,RTYPE,GRFILE,GRD,SJT,AFT
120   FORMAT(2X,6A1,2X,F7.3,1X,I2,1X,F3.1,1X,F5.2,1X,11A1,1X,1A1,
    +  2X,F3.1,3X,1A1,3X,1A1,1X,11A1,3(1X,1A1))
      GO TO 140
C
130   IERR = 1
      RETURN
C
140   READ (2,110) SETNAM
      READ (2,110) SETNAM
      CALL ATTN(1,INT(RATTN))
      CALL ATTN(2,INT(RATTN))
      RETURN
C
C     ******************************************
C     DATA READ
C
200   READ (2,210,ERR=220) SETNAM,DPKHZ,FAKHZ,FAATTN,FBKHZ,
 +              FBATTN,DBSPL,STZ,TDB
210   FORMAT  (2X,6A1,2X,F7.3,1X,F7.4,1X,F8.2,1X,F7.4,1X,F8.4,
  +        1X,F7.2,1X,F8.1,1X,F8.1)
C
220   IF (SETNAM(1) .EQ. 'S') GO TO 250
      IF (SETNAM(1) .EQ. '_') IERR = 1
      IF (IERR) CALL CLOSE (2)
      RETURN
C
250   BACKSPACE 2
      READ (2,260,ERR=300) SETNAM,RATTN,STP
260   FORMAT(2X,6A1,2X,F7.3,4X,F3.1)
C
      CALL HPCHAN ('B')
      CALL HPATTN (80.0)
      CALL HPFREQ (30.0)
      CALL HPCHAN ('A')
```

```
      CALL HPATTN (80.0)
      CALL HPFREQ (30.0)
      CALL ATTN(1,INT(RATTN))
      CALL ATTN(2,INT(RATTN))
      GO TO 200
C
300   CALL ATTN(1,127)
      CALL ATTN(2,127)
      STOP 'ERROR READING ATTENUATION AND STOP POINT'
      END
      SUBROUTINE SCFUNC(IFUN,IL,IC)
C
      BYTE CP(8),CS(4),CG(2)
C
      DATA CG /27,12/                   !CLEAR GRAPH
      DATA CS /27,'[','2','J'/          !CLEAR SCREEN
      DATA CP /27,'[','0','0',';','0','0','H'/    !POSITION CURSOR
C
C     **************************************************************
C     SUBR. STARTS
C
      GO TO (100,200,300) IFUN
C
C     SCREEN CLEAR
C
100   WRITE (5,110) CS
110   FORMAT(1X,4A1)
      RETURN
C
C     CLEAR GRAPH
C
200   WRITE (5,210) 29,CG
210   FORMAT(1X,3A1)
      RETURN
C
C     POSITION CURSOR
C
300   ENCODE (2,310,CP(3)) IL
      ENCODE (2,310,CP(6)) IC
310   FORMAT(I2)
C
      IF (CP(3) .EQ. ' ') CP(3) = '0' !REPLACE SPACE WITH ZERO
      IF (CP(6) .EQ. ' ') CP(6) = '0'
      WRITE (5,320) CP
320   FORMAT(1X,8A1,$)
C
      RETURN
      END
      SUBROUTINE SNDSET(NBRAVG,SPAN)
C
      BYTE SETNAM(6)
```

```
      BYTE OLDSET(6)      !Previous set-up name, saved.
      BYTE AVGCMD(13) !"Set number-of-averages" command.
      BYTE CFCMD(16)      !Command to establish the center frequency.
C
      BYTE SETUP(18)
C
      COMMON /COM003/ DPKHZ,FAKHZ,FAATTN,FBKHZ
      COMMON /COM010/ SETNAM,OLDSET
C
C
****************************************************************
******
C     SUBR. STARTS
C
      DO 10 I = 1,6
      IF (SETNAM(I) .NE. OLDSET(I)) GO TO 20
10    CONTINUE
C
      GO TO 350 !Dont recall same set-up.
C
20    CALL INSERT('DSFN"          ',SETUP,1,18) !ELSE, SETUP THE SETUP
      CALL INSERT(SETNAM,SETUP,6,6)
      DO 23 I = 1,6
      J = I + 5
      SETUP(J) = SETNAM(I)
23    CONTINUE
      IX = INDEX(SETUP,' ')
      CALL INSERT('";RSTA;',SETUP,IX,7)
      J = IBUP (0, 16, SETUP, 18)                    !SEND IT
C
C     SEND FREQ. SPAN
C
      ENCODE (16, 110, CFCMD) SPAN * 1000.0  !SETUP THE FREQ. SPAN
110   FORMAT ('SP ', F9.3, ' Hz;')
      J = IBUP (0, 16, CFCMD, 16)             !SEND IT
      J = IBUP (0, 16, 'FAVD;',5)
C
C     SEND NUMBER AVGS.
C
      ENCODE (13, 300, AVGCMD) NBRAVG       !SET UP # AVGS
300   FORMAT ('NAVG ', I3, ' ENT;')
      J = IBUP (0, 16, AVGCMD, 13)            !SEND IT
C
C     SAVE SETUP
C
      CALL INSERT (SETNAM,OLDSET,1,6)
C
C     SEND CENTER FREQ.
C
350   ENCODE (16, 360, CFCMD) DPKHZ * 1000.0 !MAKE ASCII STRING
360   FORMAT ('CF ', F9.3, ' Hz;')
```

```
      J = IBUP (0, 16, CFCMD, 16)          !SEND IT
C
      CALL HPCHAN ('A')              !SELECT CHANNEL A
      CALL HPFREQ (FAKHZ)                !SEND FREQ.
      CALL HPCHAN ('B')              !SAME FOR B
      CALL HPFREQ (FBKHZ)
C
      RETURN
      END
      SUBROUTINE  TCPPLT(IGS,IX,IY)
C
      DIMENSION IPLT(5)
C
      DATA IPLT /29,4*0/
C
C
***********************************************************************
C     SUBROUTINE STARTS
C
C
      ITEMP = (IY * 13) / 8        !Scale to RETROGRAPHICS
      IPLT(2) = (ITEMP / 32) + 32    !1ST Y BYTE
      IPLT(3) = MOD(ITEMP,32) + 96   !2ND Y BYTE
C
      ITEMP = (IX * 8) / 5          !AS ABOVE FOR X'S
      IPLT(4) = (ITEMP / 32) + 32
      IPLT(5) = MOD(ITEMP,32) + 64
C
C     IGS = 1 FOR GS INCLUSION (NO PLOT LINE), OR 2 FOR GS
C     EXCLUSION (DRAW A LINE).
C
      DO 500 I = IGS,5            !SEND FOR GRAPH
      CALL TEKOUT(IPLT(I))
500   CONTINUE
C
      RETURN
      END
```

COMMAND FILE TO COMPILE DPOAE

```
R FORTRA
DPOAE=DPOAE/E/W
FILXST=FILXST/E/W
RDCNFL=RDCNFL/E/W
DPPRNT=DPPRNT/E/W
GPFPRM=GPFPRM/E/W
TCPPLT=TCPPLT/E/W
SNDSET=SNDSET/E/W
DPSYN=DPSYN/E/W
DPDSPD=DPDSPD/E/W
DPIOPL=DPIOPL/E/W
DPARPL=DPARPL/E/W
DPPLT1=DPPLT1/E/W
DPPLT2=DPPLT2/E/W
PLTLIN=PLTLIN/E/W
PLTCRS=PLTCRS/E/W
PLAXIS=PLAXIS/E/W
LBLXLG=LBLXLG/E/W
DPNERR=DPNERR/E/W
SCFUNC=SCFUNC/E/W
NSFLRJ=NSFLRJ/E/W
DPPPRM=DPPPRM/E/W
MACTIT=MACTIT/E/W
DPIOEX=DPIOEX/E/W
DPAREX=DPAREX/E/W
DPVERF=DPVERF/E/W
CFRKHZ=CFRKHZ/E/W
DPIOP=DPIOP/E/W
DPARP=DPARP/E/W
DPCDFX=DPCDFX/E/W
```

COMMAND FILE TO LINK DPOAE

```
R LINK
DPOAE=DPOAE,LABLIB//
FILXST
RDCNFL
DPPRNT
GPFPRM
TCPPLT
SNDSET
DPSYN
DPDSPD
DPIOPL
DPARPL
DPPLT1
DPPLT2
PLTLIN
PLTCRS
PLAXIS
LBLXLG
DPNERR
SCFUNC
NSFLRJ
DPPPRM/O:1
MACTIT/O:1
DPIOEX/O:1
DPAREX/O:1
DPVERF/O:2
CFRKHZ/O:2
DPIOP/O:2
DPARP/O:2
DPCDFX/O:3
/ /
^C
```

DPOAE AUDIOGRAM CONTROL FILE

```
|defaults| attn  |na|stp|winsp|corfile      |nr|cr|op|pr|rt|gr file      |gr dump|
| STOP!  |10.0   | 4|0.0| 1.00|HAOPHE.COR  |Y |5.0|N|Y|-|A|HAOPHE.GPF  |Y|-----|
|--------|-------|--|---|-----|-----------|--|---|-|-|-|-|-----------|-|-----|
```

| SET-UP | DPkhz | FAkhz | FAattn | FBkhz | FBattn | dBSPL | STEPSZ | MINSPL |
|---|---|---|---|---|---|---|---|---|
| ETP0 | 0.359 | 0.455 | 13.00 | 0.551 | 13.00 | 75.0 | 10.0 | 55.0 |
| ETP0 | 0.508 | 0.643 | 13.00 | 0.778 | 13.00 | 75.0 | 10.0 | 55.0 |
| ETP0 | 0.718 | 0.909 | 13.00 | 1.100 | 13.00 | 75.0 | 10.0 | 55.0 |
| ETP0 | 0.770 | 0.975 | 13.00 | 1.180 | 13.00 | 75.0 | 10.0 | 55.0 |
| ETP0 | 0.826 | 1.045 | 13.00 | 1.264 | 13.00 | 75.0 | 10.0 | 55.0 |
| ETP0 | 0.884 | 1.119 | 13.00 | 1.354 | 13.00 | 75.0 | 10.0 | 55.0 |
| ETP0 | 0.948 | 1.200 | 13.00 | 1.452 | 13.00 | 75.0 | 10.0 | 55.0 |
| ETP0 | 1.015 | 1.285 | 13.00 | 1.555 | 13.00 | 75.0 | 10.0 | 55.0 |
| ETP0 | 1.089 | 1.378 | 13.00 | 1.667 | 13.00 | 75.0 | 10.0 | 55.0 |
| ETP0 | 1.167 | 1.477 | 13.00 | 1.787 | 13.00 | 75.0 | 10.0 | 55.0 |
| ETP0 | 1.251 | 1.583 | 13.00 | 1.915 | 13.00 | 75.0 | 10.0 | 55.0 |
| ETP0 | 1.340 | 1.696 | 13.00 | 2.052 | 13.00 | 75.0 | 10.0 | 55.0 |
| ETP0 | 1.436 | 1.818 | 13.00 | 2.200 | 13.00 | 75.0 | 10.0 | 55.0 |
| ETP0 | 1.540 | 1.949 | 13.00 | 2.358 | 13.00 | 75.0 | 10.0 | 55.0 |
| ETP0 | 1.650 | 2.088 | 13.00 | 2.526 | 13.00 | 75.0 | 10.0 | 55.0 |
| ETP0 | 1.768 | 2.238 | 13.00 | 2.708 | 13.00 | 75.0 | 10.0 | 55.0 |
| ETP0 | 1.895 | 2.399 | 13.00 | 2.903 | 13.00 | 75.0 | 10.0 | 55.0 |
| ETP0 | 2.031 | 2.571 | 13.00 | 3.111 | 13.00 | 75.0 | 10.0 | 55.0 |
| ETP0 | 2.176 | 2.755 | 13.00 | 3.334 | 13.00 | 75.0 | 10.0 | 55.0 |
| ETP0 | 2.334 | 2.954 | 13.00 | 3.574 | 13.00 | 75.0 | 10.0 | 55.0 |
| ETP0 | 2.500 | 3.165 | 13.00 | 3.830 | 13.00 | 75.0 | 10.0 | 55.0 |
| ETP0 | 2.680 | 3.393 | 13.00 | 4.106 | 13.00 | 75.0 | 10.0 | 55.0 |
| ETP0 | 2.872 | 3.636 | 13.00 | 4.400 | 13.00 | 75.0 | 10.0 | 55.0 |
| ETP0 | 3.079 | 3.897 | 13.00 | 4.715 | 13.00 | 75.0 | 10.0 | 55.0 |
| ETP0 | 3.300 | 4.177 | 13.00 | 5.054 | 13.00 | 75.0 | 10.0 | 55.0 |
| ETP0 | 3.537 | 4.477 | 13.00 | 5.417 | 13.00 | 75.0 | 10.0 | 55.0 |
| ETP0 | 3.790 | 4.798 | 13.00 | 5.806 | 13.00 | 75.0 | 10.0 | 55.0 |
| ETP0 | 4.063 | 5.143 | 13.00 | 6.223 | 13.00 | 75.0 | 10.0 | 55.0 |
| ETP0 | 4.354 | 5.512 | 13.00 | 6.670 | 13.00 | 75.0 | 10.0 | 55.0 |
| ETP0 | 4.667 | 5.907 | 13.00 | 7.147 | 13.00 | 75.0 | 10.0 | 55.0 |
| ETP0 | 5.001 | 6.331 | 13.00 | 7.661 | 13.00 | 75.0 | 10.0 | 55.0 |
| ETP0 | 5.360 | 6.785 | 13.00 | 8.210 | 13.00 | 75.0 | 10.0 | 55.0 |
| ETP0 | 5.746 | 7.273 | 13.00 | 8.800 | 13.00 | 75.0 | 10.0 | 55.0 |

CORRECTION FILE FOR DPOAE AMPLITUDE

| | |
|---|---|
| 0.500 | 4.11 |
| 0.707 | 3.46 |
| 1.000 | 1.43 |
| 1.072 | 0.46 |
| 1.149 | 0.25 |
| 1.231 | -0.01 |
| 1.320 | -0.01 |
| 1.414 | -0.17 |
| 1.516 | -0.36 |
| 1.625 | -0.52 |
| 1.741 | -0.87 |
| 1.866 | -0.87 |
| 2.000 | -0.75 |
| 2.144 | -0.40 |
| 2.297 | 0.29 |
| 2.462 | 0.46 |
| 2.639 | 0.81 |
| 2.828 | 1.31 |
| 3.031 | 2.19 |
| 3.249 | 2.60 |
| 3.482 | 3.05 |
| 3.732 | 3.56 |
| 4.000 | 4.13 |
| 4.287 | 4.61 |
| 4.595 | 5.55 |
| 4.925 | 6.44 |
| 5.278 | 8.23 |
| 5.657 | 9.51 |
| 6.063 | 10.36 |
| 6.498 | 10.48 |
| 6.964 | 9.24 |
| 7.464 | 6.92 |
| 8.000 | 5.32 |
| 999.00 | 0.00 |

AUDIOGRAM GRAPH PARAMETER FILE

```
Y
 500.
8000.
 -20.
 30.
  5.
 10.
  1.04   14.78
  1.18   14.7
  1.32   14.8
  1.46   14.62
  1.60   13.88
  1.74   13.40
  1.88   13.19
  2.02   12.6
  2.16   12.34
  2.30   11.60
  2.43   11.60
  2.57   10.91
  2.71   11.3
  2.85   11.8
  2.99   12.97
  3.13   13.67
  3.27   14.53
  3.41   15.1
  3.55   15.74
  3.69   16.57
  3.83   17.29
  3.96   17.95
  4.10   18.56
  4.24   19.28
  4.38   19.97
  4.52   20.89
  4.66   21.59
  4.80   22.42
  4.94   22.95
  5.08   23.59
  5.22   24.16
  5.36   24.74
  5.49   25.1
  5.63   25.5
  5.77   25.79
  5.91   25.95
  6.05   25.99
  6.19   25.66
  6.33   25.50
  6.47   25.30
  6.61   24.99
```

| | |
|---|---|
| 6.75 | 24.3 |
| 6.89 | 23.56 |
| 7.02 | 22.77 |
| 7.16 | 22.21 |
| 7.30 | 21.60 |
| 7.44 | 21.02 |
| 7.58 | 20.44 |
| 7.72 | 19.89 |
| 7.86 | 19.4 |
| 8.00 | 19.27 |
| 999.00 | 0.00 |
| 75 AUD AV + STD | |
| 1.04 | 3.95 |
| 1.18 | 4.79 |
| 1.32 | 5.08 |
| 1.46 | 5.26 |
| 1.60 | 4.88 |
| 1.74 | 5.02 |
| 1.88 | 4.8 |
| 2.02 | 4.6 |
| 2.16 | 3.93 |
| 2.30 | 3.70 |
| 2.43 | 2.85 |
| 2.57 | 2.84 |
| 2.71 | 2.91 |
| 2.85 | 3.38 |
| 2.99 | 3.87 |
| 3.13 | 4.57 |
| 3.27 | 5.44 |
| 3.41 | 6.18 |
| 3.55 | 6.85 |
| 3.69 | 7.48 |
| 3.83 | 8.2 |
| 3.96 | 9.13 |
| 4.10 | 9.91 |
| 4.24 | 10.6 |
| 4.38 | 11. |
| 4.52 | 11.9 |
| 4.66 | 12.3 |
| 4.80 | 12.7 |
| 4.94 | 13.3 |
| 5.08 | 13.8 |
| 5.22 | 14.4 |
| 5.36 | 14. |
| 5.49 | 15.1 |
| 5.63 | 15.0 |
| 5.77 | 15.1 |
| 5.91 | 15.2 |
| 6.05 | 15.1 |
| 6.19 | 14.6 |
| 6.33 | 14.3 |

| | |
|---|---|
| 6.47 | 13.8 |
| 6.61 | 13.3 |
| 6.75 | 12.5 |
| 6.89 | 11.8 |
| 7.02 | 11.0 |
| 7.16 | 10.6 |
| 7.30 | 10.0 |
| 7.44 | 9.44 |
| 7.58 | 8.63 |
| 7.72 | 7.8 |
| 7.86 | 7.40 |
| 8.00 | 6.38 |
| 999.00 | 0.00 |
| 75 AUD AV - STD | |
| 1.04 | 2.196 |
| 1.18 | -0.27 |
| 1.32 | -1.09 |
| 1.46 | -2.27 |
| 1.60 | -3.42 |
| 1.74 | -4.49 |
| 1.88 | -4.8 |
| 2.02 | -4.96 |
| 2.16 | -4.98 |
| 2.30 | -5.27 |
| 2.43 | -5.37 |
| 2.57 | -5.73 |
| 2.71 | -5.50 |
| 2.85 | -5.48 |
| 2.99 | -5.65 |
| 3.13 | -5.96 |
| 3.27 | -6.4 |
| 3.41 | -6.65 |
| 3.55 | -6.90 |
| 3.69 | -7.20 |
| 3.83 | -7.26 |
| 3.96 | -7.34 |
| 4.10 | -7.03 |
| 4.24 | -6.89 |
| 4.38 | -6.56 |
| 4.52 | -6.28 |
| 4.66 | -5.45 |
| 4.80 | -4. |
| 4.94 | -3.35 |
| 5.08 | -1.94 |
| 5.22 | -0.78 |
| 5.36 | 0.630 |
| 5.49 | 1.456 |
| 5.63 | 2.326 |
| 5.77 | 2.946 |
| 5.91 | 3.864 |
| 6.05 | 4.504 |

| | |
|---|---|
| 6.19 | 4.924 |
| 6.33 | 5.194 |
| 6.47 | 5.575 |
| 6.61 | 6.007 |
| 6.75 | 6.298 |
| 6.89 | 6.07 |
| 7.02 | 5.502 |
| 7.16 | 4.853 |
| 7.30 | 4.137 |
| 7.44 | 3.588 |
| 7.58 | 2.821 |
| 7.72 | 2.127 |
| 7.86 | 1.354 |
| 8.00 | 0.754 |
| 999.00 | 0.00 |
| AV AUD 75 NF + STD | |
| 1.04 | -4.514 |
| 1.18 | -4.436 |
| 1.32 | -5.682 |
| 1.46 | -6.738 |
| 1.60 | -7.372 |
| 1.74 | -7.849 |
| 1.88 | -8.410 |
| 2.02 | -8.920 |
| 2.16 | -9.217 |
| 2.30 | -9.337 |
| 2.43 | -9.378 |
| 2.57 | -9.73 |
| 2.71 | -10.03 |
| 2.85 | -10.34 |
| 2.99 | -10.34 |
| 3.13 | -10.54 |
| 3.27 | -10.54 |
| 3.41 | -10.7 |
| 3.55 | -10.81 |
| 3.69 | -10.59 |
| 3.83 | -10.74 |
| 3.96 | -11.08 |
| 4.10 | -11.08 |
| 4.24 | -11.11 |
| 4.38 | -10.74 |
| 4.52 | -10.93 |
| 4.66 | -10.77 |
| 4.80 | -10.52 |
| 4.94 | -9.462 |
| 5.08 | -8.1 |
| 5.22 | -7.411 |
| 5.36 | -7.050 |
| 5.49 | -6.652 |
| 5.63 | -5.810 |
| 5.77 | -4.346 |

| | |
|---|---|
| 5.91 | -3.340 |
| 6.05 | -2.302 |
| 6.19 | -1.833 |
| 6.33 | -1.248 |
| 6.47 | -0.993 |
| 6.61 | -0.73 |
| 6.75 | -0.329 |
| 6.89 | -0.469 |
| 7.02 | -0.32 |
| 7.16 | -0.78 |
| 7.30 | -0.836 |
| 7.44 | -1.492 |
| 7.58 | -2.270 |
| 7.72 | -2.855 |
| 7.86 | -3.337 |
| 8.00 | -3.678 |
| 999.00 | 0.00 |

AV AUD 75 NF - STD

| | |
|---|---|
| 1.04 | 9.45 |
| 1.18 | 10.5 |
| 1.32 | 11.7 |
| 1.46 | 11. |
| 1.60 | 10.5 |
| 1.74 | 9.47 |
| 1.88 | 8.28 |
| 2.02 | 7.60 |
| 2.16 | 6.92 |
| 2.30 | 6.17 |
| 2.43 | 5.4 |
| 2.57 | 5.08 |
| 2.71 | 5.15 |
| 2.85 | 5.65 |
| 2.99 | 6.18 |
| 3.13 | 6.85 |
| 3.27 | 7.63 |
| 3.41 | 8.53 |
| 3.55 | 9.77 |
| 3.69 | 10.8 |
| 3.83 | 11.6 |
| 3.96 | 12.3 |
| 4.10 | 13.1 |
| 4.24 | 13.9 |
| 4.38 | 14.8 |
| 4.52 | 15.7 |
| 4.66 | 16. |
| 4.80 | 17.3 |
| 4.94 | 17.9 |
| 5.08 | 18.5 |
| 5.22 | 18.9 |
| 5.36 | 19.5 |
| 5.49 | 19.6 |

| | |
|---|---|
| 5.36 | 5.6589 |
| 5.49 | 5.6530 |
| 5.63 | 5.0716 |
| 5.77 | 4.8986 |
| 5.91 | 4.6311 |
| 6.05 | 4.804 |
| 6.19 | 4.0090 |
| 6.33 | 3.3736 |
| 6.47 | 2.5728 |
| 6.61 | 2.2029 |
| 6.75 | 1.4426 |
| 6.89 | 1.0397 |
| 7.02 | 0.2947 |
| 7.16 | 0.1106 |
| 7.30 | -0.383 |
| 7.44 | -0.753 |
| 7.58 | -1.134 |
| 7.72 | -1.806 |
| 7.86 | -2.064 |
| 8.00 | -2.258 |
| 999.00 | 0.00 |
| AV AUD 65 - STD | |
| 1.04 | -1.7046 |
| 1.18 | -3.6785 |
| 1.32 | -5.1266 |
| 1.46 | -6.524 |
| 1.60 | -7.7620 |
| 1.74 | -8.9302 |
| 1.88 | -9.2837 |
| 2.02 | -9.0237 |
| 2.16 | -8.6558 |
| 2.30 | -9.2944 |
| 2.43 | -9.736 |
| 2.57 | -10.202 |
| 2.71 | -10.160 |
| 2.85 | -9.9322 |
| 2.99 | -9.9010 |
| 3.13 | -10.145 |
| 3.27 | -10.20 |
| 3.41 | -10.475 |
| 3.55 | -9.9642 |
| 3.69 | -9.7440 |
| 3.83 | -9.5724 |
| 3.96 | -10.373 |
| 4.10 | -10.9 |
| 4.24 | -11.172 |
| 4.38 | -11.000 |
| 4.52 | -10.433 |
| 4.66 | -10.178 |
| 4.80 | -9.7236 |
| 4.94 | -9.5813 |

| | |
|---|---|
| 5.63 | 19. |
| 5.77 | 19.7 |
| 5.91 | 19.9 |
| 6.05 | 19.9 |
| 6.19 | 19.8 |
| 6.33 | 19.3 |
| 6.47 | 19.1 |
| 6.61 | 18.8 |
| 6.75 | 18.3 |
| 6.89 | 17.6 |
| 7.02 | 17.0 |
| 7.16 | 16.3 |
| 7.30 | 15.5 |
| 7.44 | 14.5 |
| 7.58 | 13.9 |
| 7.72 | 13.2 |
| 7.86 | 12.7 |
| 8.00 | 12.2 |
| 999.00 | 0.00 |
| 65 AUD AV + STD | |
| 1.04 | 1.8420 |
| 1.18 | 1.8145 |
| 1.32 | 1.162 |
| 1.46 | 0.3147 |
| 1.60 | -0.569 |
| 1.74 | -1.6 |
| 1.88 | -2.25 |
| 2.02 | -3.022 |
| 2.16 | -3.896 |
| 2.30 | -5.14 |
| 2.43 | -5.77 |
| 2.57 | -6.138 |
| 2.71 | -5.923 |
| 2.85 | -5.086 |
| 2.99 | -4.400 |
| 3.13 | -3.662 |
| 3.27 | -2.932 |
| 3.41 | -2.361 |
| 3.55 | -1.310 |
| 3.69 | -0.637 |
| 3.83 | 0.3586 |
| 3.96 | 0.9347 |
| 4.10 | 1.4888 |
| 4.24 | 2.1902 |
| 4.38 | 2.5201 |
| 4.52 | 3.1214 |
| 4.66 | 3.7868 |
| 4.80 | 4.4896 |
| 4.94 | 5.1108 |
| 5.08 | 5.2629 |
| 5.22 | 5.5657 |

| | |
|---|---|
| 5.08 | -8.8902 |
| 5.22 | -8.1826 |
| 5.36 | -7.3070 |
| 5.49 | -6.754 |
| 5.63 | -6.0291 |
| 5.77 | -5.3078 |
| 5.91 | -4.7311 |
| 6.05 | -4.2696 |
| 6.19 | -3.9666 |
| 6.33 | -3.2263 |
| 6.47 | -2.6605 |
| 6.61 | -2.6382 |
| 6.75 | -2.6249 |
| 6.89 | -2.7753 |
| 7.02 | -2.9708 |
| 7.16 | -3.3507 |
| 7.30 | -4.0275 |
| 7.44 | -4.7458 |
| 7.58 | -5.2700 |
| 7.72 | -5.9322 |
| 7.86 | -6.611 |
| 8.00 | -6.4885 |
| 999.00 | 0.00 |
| AV AUD 65 NF + STD | |
| 1.04 | -9.193 |
| 1.18 | -8.778 |
| 1.32 | -9.883 |
| 1.46 | -11.54 |
| 1.60 | -12.60 |
| 1.74 | -12. |
| 1.88 | -12.91 |
| 2.02 | -13.49 |
| 2.16 | -14.10 |
| 2.30 | -14.43 |
| 2.43 | -14.31 |
| 2.57 | -13.86 |
| 2.71 | -13.55 |
| 2.85 | -13.69 |
| 2.99 | -13.53 |
| 3.13 | -13.71 |
| 3.27 | -13.57 |
| 3.41 | -13.73 |
| 3.55 | -13.66 |
| 3.69 | -13.74 |
| 3.83 | -13.68 |
| 3.96 | -13.53 |
| 4.10 | -13.68 |
| 4.24 | -13.68 |
| 4.38 | -13.61 |
| 4.52 | -13.42 |
| 4.66 | -13.04 |

| | |
|---|---|
| 4.80 | -12.8 |
| 4.94 | -12.40 |
| 5.08 | -11.93 |
| 5.22 | -11.20 |
| 5.36 | -10.54 |
| 5.49 | -10.09 |
| 5.63 | -9.753 |
| 5.77 | -9.066 |
| 5.91 | -8.426 |
| 6.05 | -7.814 |
| 6.19 | -7.370 |
| 6.33 | -7.260 |
| 6.47 | -7.166 |
| 6.61 | -7.017 |
| 6.75 | -6.845 |
| 6.89 | -6.773 |
| 7.02 | -7.064 |
| 7.16 | -7.736 |
| 7.30 | -8.499 |
| 7.44 | -8.863 |
| 7.58 | -9.288 |
| 7.72 | -9.498 |
| 7.86 | -9.852 |
| 8.00 | -11.15 |
| 999.00 | 0.00 |

AV AUD 65 NF - STD

| | |
|---|---|
| 0.999 | 8.82 |
| 1.230 | 8.43 |
| 1.513 | 5.73 |
| 1.863 | 4.16 |
| 2.292 | 3.92 |
| 2.822 | 3.56 |
| 3.475 | 4.95 |
| 4.277 | 8.60 |
| 5.265 | 11.24 |
| 6.482 | 9.79 |
| 7.980 | 2.40 |
| 999.00 | 0.00 |

AV AUD 55 + STD

| | |
|---|---|
| 0.999 | -2.18 |
| 1.230 | -1.18 |
| 1.513 | -4.58 |
| 1.863 | -6.43 |
| 2.292 | -11.14 |
| 2.822 | -8.32 |
| 3.475 | -7.76 |
| 4.277 | -5.08 |
| 5.265 | -1.36 |
| 6.482 | -2.03 |

| | |
|---|---|
| 7.980 | -7.34 |
| 999.00 | 0.00 |

AV AUD 55 - STD

| | |
|---|---|
| 0.999 | 2.47 |
| 1.230 | 0.87 |
| 1.513 | -7.98 |
| 1.863 | -9.63 |
| 2.292 | -10.70 |
| 2.822 | -5.75 |
| 3.475 | -9.44 |
| 4.277 | -12.60 |
| 5.265 | -10.19 |
| 6.482 | -5.91 |
| 7.980 | -10.25 |
| 999.00 | 0.00 |

AV AUD 55 NF + STD

| | |
|---|---|
| 0.999 | -9.40 |
| 1.230 | -10.73 |
| 1.513 | -13.92 |
| 1.863 | -15.62 |
| 2.292 | -15.32 |
| 2.822 | -16.26 |
| 3.475 | -15.05 |
| 4.277 | -15.30 |
| 5.265 | -12.40 |
| 6.482 | -10.36 |
| 7.980 | -13.23 |
| 999.00 | 0.00 |

AV AUD 55 + STD

I/O CONTROL FILE

```
________________________________________________________________________________
__________
|defaults| attn   |na|stp|winsp|corfile      |nr|cr|op|pr|rt|gr file      |gr dump|
| STOP!  |10.0    | 4|3.0| 1.00|HIAPHE.COR |Y |5.0|N|Y|-|I|HIAPHE.GPF |Y|-----|
|--------|-------|--|---|-----|-----------|--|---|-|-|-|-|-----------|-|---
--|
| SET-UP | DPkhz | FAkhz | FAattn | FBkhz | FBattn | dBSPL | STEPSZ | MINSPL |
| ETP0   | 0.359 | 0.455 |   3.00 | 0.551 |  3.00  |  85.0 |    5.0 |   25.0 |
| ETP0   | 0.718 | 0.909 |   3.00 | 1.100 |  3.00  |  85.0 |    5.0 |   25.0 |
| ETP0   | 1.436 | 1.818 |   3.00 | 2.200 |  3.00  |  85.0 |    5.0 |   25.0 |
| ETP0   | 2.154 | 2.727 |   3.00 | 3.300 |  3.00  |  85.0 |    5.0 |   25.0 |
| ETP0   | 2.872 | 3.636 |   3.00 | 4.400 |  3.00  |  85.0 |    5.0 |   25.0 |
| STOP!  |10.0   | 4|0.0||       |       |        |       |
| ETP0   | 4.309 | 5.455 |   3.00 | 6.601 |  3.00  |  85.0 |    5.0 |   25.0 |
| ETP0   | 5.746 | 7.273 |   3.00 | 8.800 |  3.00  |  85.0 |    5.0 |   25.0 |
|________|_______|_______|________|_______|________|_______|________|___
_____|
```

I/O CORRECTION FILE

| | |
|---|---|
| 0.50 | 4.11 |
| 1.00 | 1.43 |
| 2.00 | -0.75 |
| 3.00 | 2.19 |
| 4.00 | 4.13 |
| 6.00 | 10.32 |
| 8.00 | 5.32 |
| 999.00 | 0.00 |

I/O GRAPH PARAMETER FILE

```
N
  25.
  85.
  -20.
  30.
   1.
  10.
   1.
  10.
```

What is claimed is:

1. Distortion product emission apparatus comprising, signal generating means for generating a first electrical signal of frequency $f_1$ and a second electrical signal of frequency $f_2$, the frequency $f_2$ being greater than the frequency $f_1$, first and second earphones responsive respectively to said first and second electrical signals for producing a first tone of frequency $f_1$ and a second tone of frequency $f_2$, an eartip arranged and designed insertion in the ear canal of the outer ear of a human being, said eartip having first and second audio tubes terminated therein which are connected respectively to said first and second earphones which transmit said first tone and said second tone to said ear, said eartip including a first microphone means with a first output lead connected thereto for generating a first electrical signal on said first output lead which is proportional to a distortion product emission tone generated in the ear of said human being at a frequency of $2_{f1}$–$f_2$ and to other body noises, said eartip including a second microphone means with a second output lead connected thereto for generating a second electrical signal on said second output lead which is proportional to said other body noises but is not substantially proportional to distortion product emission tone generated in the ear of said human being at a frequency of $2_{f1}$–$f_2$, differential amplifier means responsive to said first and second signals for generating a differential signal proportional to the differences between said first and second electrical signals on a third output lead on which said distortion product emission tone at a frequency of $2f_1$–$f_2$ is present, but noise signals due to body noises of said human being have been reduced, and signal analyzing means responsive to said differential signal on said third output lead for generating a level signal corresponding to said distortion product emission tone generated in the ear of said human being at a frequency of $2f_1$–$f_2$.

2. The apparatus of claim 1 further comprising, digital computer means for controlling said signal generating means to produce a plurality of sets of signals of frequency $f_1$ and $f_2$ where the ratio of such frequencies $f_2/f_1$ is approximately the same for each set of signals, and responsive to said signal analyzing means for recording each level of said tone at frequency $2f_1$–$f_2$ corresponding to each of said sets of frequencies $f_1$, $f_2$.

3. Distortion product emission apparatus comprising, signal generating means for generating a first electrical signal of frequency $f_1$ and a second electrical signal of frequency $f_2$, the frequency $f_2$ being greater than the frequency $f_1$, said first and second signals having substantially equal amplitude levels, first and second earphones responsive respectively to said first and second electrical signals for producing a first tone of frequency $f_1$ and a second tone of frequency $f_2$, an eartip arranged and designed insertion in the ear canal of the outer ear of an human being, said eartip having first and second audio tubes terminated therein which are connected respectively to said first and second earphones which transmit said first tone and said second tone to said ear, said eartip including a first microphone of high signal sensitivity with a first output lead connected thereto, and a second microphone of low signal sensitivity with a second output lead connected thereto, said first microphone being sensitive to small amplitude DPE signals of frequency $2f_1$–$f_2$ and to contaminating large amplitude signals caused by coughs and the like whereas said second microphone is not sensitive to said small amplitude DPE signals of frequency $2f_1$–$f_2$ but is sensitive to said large amplitude body-induced signals, differential amplifier means having positive and negative input terminals to which said first output lead and said second output leads are connected for subtracting the respective signals on said first and second output leads to produce a DPE signal on an output lead with reduced contamination due to said large amplitude signals.

4. The apparatus of claim 3 further comprising gain adjusting circuit means between said second output lead of said second microphone and said differential amplifier means for manual adjustment of the amplitude of large amplitude signals sensed by said second microphone.

5. The apparatus of claim 4 further comprising phase adjusting circuit means between said second output lead of said second microphone and said differential amplifier means for manual adjustment of the phase of large amplitude signals sensed by said second microphone.

6. Distortion product emission apparatus comprising, signal generating means for generating a first steady state oscillating signal of frequency $f_1$, and a second steady state oscillating signal of frequency $f_2$, the frequency $f_2$ being greater than the frequency $f_1$, said first and second signals having substantially equal amplitude levels, means for synchronizing said first and second signals such that there is substantially no phase drift between said first and second signals, first and second earphones responsive respectively to said first and second signals for producing a first tone of frequency $f_1$ and a second tone of frequency $f_2$, an eartip arranged and designed for insertion in the ear canal of the outer ear of a human being, said eartip having first and second audio tubes which are connected respectively to said first and second earphones which transmit said first tone and said second tone to said ear, said eartip including a microphone with a first output lead connected thereto, said microphone generating an output signal on said first output lead which includes random phase noise and a steady state oscillating distortion product emission (DPE) tone generated in the ear of said human being, said distortion product emission (DPE) tone being a sinusoid of substantially constant amplitude and phase with a frequency of $2f_1$–$f_2$, means coupled to said signal generating means for generating a triggering signal which is of substantially the same frequency and phase as that of said DPE tone of said output signal, a signal analyzer including (i) time averaging means for time averaging said output signal prior to spectral analysis of said output signal, said time averaging means including means responsive to said output signal and to said triggering signal for time averaging said output signal by separating said output signal into a plurality of equal length time segments such that the DPE tone component of frequency $2f_1$–$f_2$ of said output signal begins with the same phase in each time segment, and means for averaging said equal length time segments to produce an averaged signal, and (ii) a Fourier-transform spectrum analyzer means responsive to said averaged signal for determining the amplitude versus frequency spectrum of said averaged signal, whereby said amplitude at said frequency $2f_1-f_2$ substantially represents the level of the DPE tone and the noise level is substantially reduced.

7. The apparatus of claim 6 further comprising, digital computer means for controlling said signal generating means to produce a plurality of sets of signals of frequency $f_1$ and $f_2$ where the ratio of such frequencies $f_2/f_1$ is approximately the same for each set of signals, and responsive to said signal analyzing means for recording each level of said tone at frequency of $2f_1-f_2$ corresponding to each of said sets of frequencies $f_1$, $f_2$.

8. A method for reducing noise in distortion product emission testing comprising the steps of generating a first steady state oscillating signal of frequency $f_1$ and a second steady state oscillating signal of frequency $f_2$ and a triggering signal of frequency $2f_1-f_2$ such that said first signal, said second signal and said triggering signal have substantially no phase drift among any of such signals, applying said first steady state oscillating signal of frequency $f_1$ and said second steady state oscillating signal of frequency $f_2$ to the ear canal of the outer ear of a human being, generating a steady state electrical response signal representative of the distortion product emission tone (DPE) of substantially constant amplitude and phase of frequency $2f_1-f_2$ which is generated in the ear in response to said first and second signals, said steady state electrical response signal being contaminated by random phase noise, dividing said steady state electrical response signal by reference to said triggering signal into a plurality of equal length time segment DPE signals such that each DPE signal of frequency $2f_1-f_2$ begins with the same phase, averaging said DPE signals over a predetermined number of time segments to produce an averaged signal, and applying said averaged signal to a Fourier-transform spectrum analyzer to determine the amplitude level versus DPE frequency spectrum of said averaged signal, whereby said amplitude at said frequency $2f_1-f_2$ substantially represents the level of said DPE tone and the noise level is substantially reduced.

9. Distortion product emission apparatus comprising, first signal generating means for generating a first electrical signal of frequency $f_1$ and a second electrical signal of frequency $f_2$, the frequency $f_2$ being greater than the frequency $f_1$, such that the phase of the first and second signals do not substantially drift with respect to each other, second signal generating means for generating an oscillating triggering signal of frequency $2f_1-f_2$, the phase of which does not substantially drift from that of said first electrical signal of frequency $f_1$ or that of said second electrical signal of frequency $f_2$, first and second earphones responsive respectively to said first and second electrical signals for producing a first tone of frequency $f_1$ and a second tone of frequency $f_2$, an eartip arranged and designed for insertion in the ear canal of the outer ear of a human being, said eartip having first and second audio tubes which are connected respectively to said first and second earphones which transmit said first tone and said second tone to said ear, said eartip including a microphone with a first output lead connected thereto, said microphone generating an electrical signal on said first output lead which includes random phase noise and a distortion product emission tone being a sinusoid of substantially constant amplitude and phase with a frequency of $2f_1-f_2$, a signal processor including (i) time averaging means responsive to positive going zero crossing times of said triggering signal for time averaging said signal on said first output lead by separating said signal into a plurality of equal length time segments such that the distortion product emission tone of said signal begins with the same phase in each time segment and averaging said equal length time segments to produce an averaged signal, and (ii) a spectral analyzer including a Fourier-transform spectrum analyzer, and means for applying said averaged signal to said Fourier-transform spectrum analyzer for determining an amplitude versus frequency spectrum of said averaged signal, whereby said amplitude at said frequency $2f_1-f_2$ substantially represents the level of said distortion product emission tone and the noise level is substantially reduced.

10. Distortion product emission apparatus comprising, signal generating means for generating a first electrical sinusoidal signal of frequency $f_1$, a second electrical sinusoidal signal of frequency $f_2$ and a third electrical square-wave signal of frequency $2f_1-f_2$, where said first, second and third signals have substantially no phase drift among them, first and second earphones responsive respectively to said first and second electrical signals for producing a first tone of frequency $f_1$ and a second tone of frequency $f_2$, an eartip adapted for insertion in the ear canal of the outer ear of a human being, said eartip having first and second audio tubes which are connected respectively to said first and second earphones which transmit said first tone and said second tone to said ear, said eartip including a microphone with a first output lead connected thereto, said microphone generating a fourth electrical signal on said first output lead which includes random phase noise and a distortion product emission tone generated in the ear of said human being, said distortion product emission tone being a sinusoid of substantially constant amplitude and phase with a frequency of $2f_1-f_2$, signal processing means for (a) producing from said fourth electrical signal a plurality of time segments such that each time segment of frequency $2f_1-f_2$ begins with the same phase, (b) averaging over a predetermined number of said time segments of said fourth electrical signal to produce an averaged signal, and (c) applying said averaged signal to a spectrum analyzer for determining the amplitude versus frequency spectrum of said averaged signal, whereby said amplitude at said frequency $2f_1-f_2$ substantially represents the level of said distortion product emission tone and the noise level at other frequencies is substantially reduced, said spectrum analyzer means including a trigger input and a signal input, wherein said first output lead is connected to said signal input of said spectrum analyzer and said third electrical square wave signal of frequency $2f_1-f_2$ is applied to said trigger input.

11. A method for reducing noise in distortion product emission testing comprising the steps of:

generating a steady state electrical signal representative of the distortion product emission (DPE) tone from an ear, said DPE tone being of constant amplitude, frequency and phase, said steady state electrical signal being contaminated by random phase noise, repeatedly initiating a time sample having a length which does not drift with respect to the period of said DPE tone to produce a plurality of time samples, producing an averaged signal by averaging segments of said steady-state electrical signal which occur in said time samples; and applying said averaged signal to a Fourier-transform spectrum analyzer to determine the amplitude level of said DPE tone of said averaged signal, whereby noise is reduced.

12. The method of claim 11 wherein said generating step includes the substeps of generating a first signal of frequency $f_1$ and a second signal of frequency $f_2$ such that the phase of said first and second signals do not drift with respect to each other, and said first and second signals are of substantially constant amplitude and substantially constant frequency, and applying said first and second signals to an ear, whereby said ear produces said DPE tone in response thereto of constant frequency $2f_1-f_2$ and of a phase which does not drift with respect to the phase of said first signal or to the phase of said second signal.

13. The method of claim 12 further comprising the steps of generating a triggering signal of frequency $2f_1-f_2$ having a phase which does not substantially drift from the phase of said first signal or from the phase of said second signal, and controlling the beginning of said time samples in said initiating step to coincide with a positive going zero crossing time of said triggering signal.

* * * * *